US009931325B2

(12) United States Patent
Forbes et al.

(10) Patent No.: US 9,931,325 B2
(45) Date of Patent: Apr. 3, 2018

(54) METHODS FOR TREATING IRRITABLE BOWEL SYNDROME (IBS)

(71) Applicant: Salix Pharmaceuticals, Ltd., Bridgewater, NJ (US)

(72) Inventors: William Forbes, Raleigh, NC (US); Enoch Bortey, Chapel Hill, NC (US)

(73) Assignee: Salix Pharmaceuticals, Ltd., Bridgewater, NJ (US)

( * ) Notice: Subject to any disclaimer, the term of this patent is extended or adjusted under 35 U.S.C. 154(b) by 0 days.

(21) Appl. No.: 15/398,283

(22) Filed: Jan. 4, 2017

(65) Prior Publication Data
US 2017/0182013 A1    Jun. 29, 2017

Related U.S. Application Data

(63) Continuation of application No. 13/755,578, filed on Jan. 31, 2013, now Pat. No. 9,566,270, which is a continuation of application No. 12/880,739, filed on Sep. 13, 2010, now abandoned, which is a continuation-in-part of application No. 12/393,979, filed on Feb. 26, 2009, now Pat. No. 8,309,569.

(60) Provisional application No. 61/031,679, filed on Feb. 26, 2008, provisional application No. 61/102,801, filed on Oct. 13, 2008, provisional application No. 61/241,945, filed on Sep. 13, 2009, provisional application No. 61/262,475, filed on Nov. 18, 2009, provisional application No. 61/329,511, filed on Apr. 29, 2010.

(51) Int. Cl.
*A61K 31/415*    (2006.01)
*A61K 31/34*    (2006.01)
*A61K 31/437*    (2006.01)

(52) U.S. Cl.
CPC ................... *A61K 31/437* (2013.01)

(58) Field of Classification Search
USPC .................................... 514/393, 468
See application file for complete search history.

(56) References Cited

U.S. PATENT DOCUMENTS

| | | | |
|---|---|---|---|
| 7,915,275 | B2 | 3/2011 | Viscomi et al. |
| 8,309,569 | B2 | 11/2012 | Forbes et al. |
| 2005/0272754 | A1 | 12/2005 | Viscomi et al. |
| 2006/0029550 | A1 | 2/2006 | Lin et al. |
| 2007/0259906 | A1 | 11/2007 | Caras |
| 2008/0132530 | A1 | 6/2008 | Viscomi et al. |
| 2009/0012113 | A1 | 1/2009 | Lin et al. |
| 2009/0028940 | A1 | 1/2009 | Jahagirdar et al. |
| 2009/0192083 | A1 | 7/2009 | Currie |
| 2010/0136125 | A1 | 6/2010 | Jacobus et al. |

FOREIGN PATENT DOCUMENTS

| | | |
|---|---|---|
| KR | 100137810 | 2/1998 |
| WO | 2006094737 A2 | 9/2006 |
| WO | 2007/064964 A2 | 6/2007 |
| WO | 2009108814 A1 | 9/2009 |

OTHER PUBLICATIONS

Taylor et al. "Systemic Pharmacokinetics of Rifaximin in Volunteers with Shigellosis"; Mar. 2008 (Mar. 2008) Antimicrobial Agents and Chemotherapy, vol. 52, No. 3; p. 1179-1181; table 1; p. 1179, col. 1, para 1, col. 2, para 1; p. 1180, col. 1, para 1; p. 1181, col. 1, para 1-2.
Gionchetti et. al. "Antibiotic treatment in inflammatory bowel disease; rifaximin a new possible approach"; European Review for Medical and Pharmacological Sciences; 1999; vol. 3; p. 27-30.; p. 29, col. 1, para 1.
Vignali et al. "TIPS with Expanded Polytetrafluoroethylene-Covered Stent: Results of an Italian Multicenter Study"; Aug. 2005 (Aug. 2005) American Roentgen Ray Society, 185;472-480; table 1, figure 5, abstract; p. 474, col. 1, para 2; p. 478, col. 3, para 1.
Chari et al. "Treatment of Hepatic Failure with ex Vivo Pig-Liver Perfusion Followed by Liver Transplantation"; Jul. 28, 1994 (Jul. 28, 1994) The New England Journal of Medicine vol. 331, n 4; p. 235, col. 1, para 1, col. 2, para 1; p. 236, col. 2, para 1.
Pimentel et al. "The Effect of a Nonabsorbed Oral Antibiotic (Rifaximin) on the Symptoms of the Irritable Bowel Syndrome" Annals of InternalMedicine. vol. 145, Issue 8, p. 557-563, Oct. 17, 2006.
Salix Pharmaceuticals "Study to Assess the Efficacy and Safety of Rifaximin Administered BID in the Treatment of Patients With Diarrhea-Associated Irritable Bowel Syndrome" Dec. 6, 2007, <http://clinicaltrials.gov/ct2/show/NCT00269412>, p. 1,para 1.
DuPont et al. "Rifaximin: A Nonabsorbed Antimicrobial in the Therapy of Travelers Diarrhea" Digestion. vol. 59, Issue 3, pp. 708-714 especially abstract, Nov. 1998.
Shahara et al. "Randomized Double-Blind Placebo-Controlled Trial of Rifaximin in Patients with Abdominal Bloating and Flatulence" American Journal of Gastroenterology. vol. 101, Issue 2, p. 326-333, Feb. 2006.
Lauritano et al. "Association between Hypothyroidism and Small Intentinal Bacterial Overgrowth" The journal of Clinical Endrocrinology & Metabolism. vol. 92, Issue 11, pp. 4180-4184 especially p. 4181. Nov. 2007.
Miglio, F., et al , "Rifaximin, A Non-Absorbable Rifamycin, for the Treatment of Hepatic Encephalopathy. A Double-Blind, Randomised Trial" Curr. Med. Res. Opin., 1997; 13(10), p. 593-601, PMID: 9327194 (Abstract Only).
Scarpellini, E., et al., "High Dosage Rifaximin for the Treatment of Small Intestinal Bacterial Overgrowth" Aliment Pharmacol Ther., Apr. 1, 2007; 25(7), p. 781-786.

(Continued)

*Primary Examiner* — Jeffrey S Lundgren
*Assistant Examiner* — Michael J Schmitt
(74) *Attorney, Agent, or Firm* — McCarter & English, LLP; Jonathan M. Sparks; Michael J. DeGrazia

(57) ABSTRACT

The present invention provides new methods and kits for treating IBS; treating IBS in females; treating IBS in older subjects; and treating IBS in non-white subjects.

9 Claims, 13 Drawing Sheets

(56) References Cited

OTHER PUBLICATIONS

Gordon, S., et al., "Validation of Irritable Bowel Syndrome Global Improvement Scale: An Integrated Symptom End Joint for Assessing Treatment Efficacy" Dig. Dis. Sci., 2003; 48(7), p. 1317-23 PMID: 12870789 (Abstract Only).

Mintz, et al., Ocular Manifestations of Inflammatory Bowel Disease, Inflammatory Bowel Diseases, vol. 20, Issue 2, pp. 13-139, Mar., 24.

Pimental, Mark, et al., "A 10-day Course of Rifaximin, A Non-Absorbable Antibiotic, Produces a Durable Improvement in All Symptoms of Irritable Bowel Syndrome: A Double-Blind Randomized Controlled Study," Gastroenterology, vol. 130, No. 4, Suppl. 2, Apr. 2006, p. A26, XP002718616.

Frissora, C.L., et al., "Review Article: The Role of Antibiotics vs. Conventional Pharmacotherapy in Treating Symptoms of Irritable Bowel Syndrome," Alimentary Pharmacology & Therapeutics, vol. 25, No. 11, Jun. 1, 2007, pp. 1271-1281.

"Rifaximin Demonstrates Statistically Significant Improvement in Co-Primary Endpoints in Treatment of Diarrhea-Associated Irritable Bowel Syndrome in Phase 11b Study," URL:http://www.drugs.com/clinical_trials/rifaximin-demonstrates-statistically-significant-improvement-co-primary-endpoints-diarrhea-1851.html, Sep. 2007, XP002718618.

Steffen, Robert, et al., "Therapy of Travelers' Diarrhea with Rifaximin on Various Continents," The American Journal of Gastroenterology, May 5, 2003, vol. 98, No. 5, pp. 1073-1078.

Bass, N.M., "Review Article: The Current Pharmacological Therapies for Hepatic Encephalopathy," Alimentary Pharmacology & Therapeutics, Blackwell Scientific Publications Ltd, Cambridge, GB, vol. 25, No. Suppl. 1, Feb. 1, 2007, pp. 23-31.

Frissora, Christine, "Premenstrual Syndrome Exacerbates Irritable Bowel Syndrome (PMS-IBS): Can the Nonsystemic Antibiotic Rifaximin Alleviate Cyclical Symptoms of Bloating, Abdominal Discomfort, and Diarrhea in Women?" American Journal of Gastroenterology, vol. 103, No. Suppl. S, Sep. 2008, pp. S463-S464, XP002688387.

"Abstracts of the AGA Institute," Gastroenterology, Elsevier, Philadelphia, PA, vol. 130, No. 4, Apr. 1, 2006, pp. A1-A26, Abstract 134, XP005643844.

Marchina, M., "Infectious Diarrhea in the Aged: Controlled Clinical Trial of Rifaximin" Chemioterapta, vol. 7, No. 5, pp. 336-340, 1988.

Scarpignato, C., et al., "Rifaximin, a Poorly Absorbed Antibiotic: Pharmacology and Clinical Potential" Chemotherapy, 2005:51(suppl. 1):36-66.

Tillisch, et al., "Characterization of the Alternating Bowel Habit Subtype in Patients with Irritable Bowel Syndrome," The American Journal of Gastroenterology, vol. 100, No. 4, Apr. 1, 2005, pp. 896-904 (XP055175635).

Adachi, J.A., "Rifaximin: A Novel Nonabsorbed Rifamycin for Gastrointestinal Disorders," Reviews of Anti-Infective Agents, 42, pp. 541-547, 2006.

Lawrence, K.R., et al., "Rifaximin for the Treatment of Hepatic Encephalopathy," Pharmacotherapy, 28(8), pp. 1019-1032, 2008.

de Melo, R.T., et al., "Rifaximin for the Treatment of Hepatic Encephalopathy," Am J Health-Syst Pharm, vol. 65, pp. 318-822, 2008.

Brigidi et al., "Effects of rifaximin administration on the intestinal microbiota in patients with ulcerative colitis," Journal of Chemotherapy. 14(3): 290-5 (2002).

Vaira et al., "Rifaximin suspension for the eradication of helicobacter pylori." Current Therapeutic Research. 58(5): 300-8 (1997).

Impact of Rifaximin on Relief of IBS Symptoms at Month 1

METHODS FOR TREATING IRRITABLE BOWEL SYNDROME (IBS)

RELATED APPLICATIONS

This application is a continuation of U.S. Ser. No. 13/755,578 filed 31 Jan. 2013; which is a continuation of Ser. No. 12/880,739 filed 13 Sep. 2010; which claims the benefit of U.S. 61/241,945 filed 13 Sep. 2009, U.S. 61/262,475 filed 18 Nov. 2009, and U.S. 61/329,511 filed 29 Apr. 2010; and U.S. Ser. No. 12/880,739 is a CIP of Ser. No. 12/393,979 filed 26 Feb. 2009, which claims the benefit of U.S. 61/031,679 filed 26 Feb. 2008 and 61/102,801 filed 3 Oct. 2008; the entire contents of which are expressly incorporated herein by reference.

BACKGROUND

Rifaximin (INN; see The Merck Index, XIII Ed., 8304) is an antibiotic belonging to the rifamycin class of antibiotics, e.g., a pyrido-imidazo rifamycin. Rifaximin exerts its broad antibacterial activity, for example, in the gastrointestinal tract against localized gastrointestinal bacteria that cause infectious diarrhea, irritable bowel syndrome, small intestinal bacterial overgrowth, Crohn's disease, and/or pancreatic insufficiency. It has been reported that rifaximin is characterized by a negligible systemic absorption, due to its chemical and physical characteristics (Descombe J. J. et al. *Pharmacokinetic study of rifaximin after oral administration in healthy volunteers. Int J Clin Pharmacol Res,* 14 (2), 51-56, (1994)).

SUMMARY

Disclosed herein are methods of preventing, ameliorating and/or treating bowel diseases (BDs). In general, subjects who may benefit from treatment with a rifamycin class antibiotic (e.g., rifaximin) include those who are susceptible to BDs, those who have active or acute diseases and those who are in remission from one or more BDs. BDs include, for example, irritable bowel syndrome (IBS), diarrhea-predominant Irritable Bowel Syndrome (dIBS), Crohn's disease, traveler's diarrhea, ulcerative colitis, enteritis, small intestinal bacterial overgrowth, chronic pancreatitis, pancreatic insufficiency, colitis, diverticular disease and/or hepatic encephalopathy. Subjects who may particularly benefit from this treatment include those who are or may be suffering from or susceptible to IBS.

In one aspect, presented herein are methods of treating bowel disease (BD) with a durability of antibiotic response, comprising administering a therapeutically effective amount of a rifamycin class antibiotic to a subject in need thereof, selecting subjects who respond to treatment after being treated for between about 1 and about 24 weeks, and removing a responding subject from treatment wherein after removal of treatment there is a durability of response.

In one aspect, presented herein are methods of treating bowel disease (BD), comprising administering to a subject in need thereof 550 mg of rifaximin TID, thereby treating BD.

In one embodiment, the bowel disease comprises Irritable Bowel Syndrome (IBS).

In one embodiment, the bowel disease comprises diarrhea-associated Irritable Bowel Syndrome (dIBS).

In one embodiment, the bowel disease comprises hepatic encephalopathy.

In another embodiment, hepatic encephalopathy (HE) will be administered a rifamycin class antibiotic for between about 28 days weeks and 24 months. In treating HE, the rifamycin class antibiotic may be administered for as long a necessary, for example, for 12 months and longer, or for a subject's entire life span, for example, after being suspected of or diagnosed as having HE.

In one embodiment, at least 50% of patients respond.

In one embodiment, the therapeutically effective amount comprises from between about 25 mg to about 6000 mg.

In one embodiment, the therapeutically effective amount comprises 550 mg TID.

In one embodiment, the therapeutically effective amount comprises 550 mg BID.

In one embodiment, the therapeutically effective amount comprises 600 mg TID.

In one embodiment, the therapeutically effective amount comprises 600 mg BID.

In one embodiment, the therapeutically effective amount comprises 1650 mg/day.

In one embodiment, the BD comprises diarrhea-predominant irritable bowel syndrome (dIBS). In one embodiment, the BD comprises alternating-predominant irritable bowel syndrome.

In one embodiment, the rifamycin class antibiotic comprises a compound of Formula I.

In one embodiment, the rifamycin class antibiotic comprises rifaximin. In one embodiment, the BD comprises alternating-predominant irritable bowel syndrome.

In one embodiment, subjects are treated from between about 7 days and about 4 weeks prior to selection.

In one embodiment, the subject is selected upon response to the rifamycin class antibiotic.

In one embodiment, the subject is selected when response to the rifamycin class antibiotic is recognized.

In one embodiment, the durability of response comprises from at least between about 1 and about 24 weeks of adequate relief of symptoms.

In one embodiment, the durability of response comprises from at least between about 1 and about 5 weeks of adequate relief of symptoms.

In one embodiment, symptoms comprise one or more of overall BD symptoms or bloating.

In one embodiment, adequate relief of BD symptoms comprises a reduction of BD symptoms.

In one embodiment, the reduction in BD symptoms is a reduction from baseline symptoms.

In one embodiment, baseline symptoms are established prior to treatment.

In one embodiment, adequate relief of BD symptoms comprises a 'yes' response from a subject when asked the question comprising or similar to, "In the past 7 days, have you had adequate relief of your symptom of your BD symptoms?" In one embodiment, adequate relief of BD symptoms comprises an affirmative response (e.g., yes) from a subject if asked weather they have had adequate relief of symptom of BD.

In one embodiment, BD symptoms comprise one or more of cramping, pain, diarrhea, constipation, lumpy stool, watery stool, frequent stool production, abdominal pain, abdominal discomfort, and/or urgency.

In one embodiment, wherein adequate relief of bloating symptoms comprises a reduction of bloating symptoms.

In one embodiment, wherein the reduction in bloating symptoms is a reduction from baseline symptoms.

In one embodiment, baseline symptoms are established prior to treatment.

In one embodiment, adequate relief of bloating symptoms comprises a 'yes' response from a subject when asked the question comprising or similar to "In the past 7 days, have you had adequate relief of your symptom of bloating?" In one embodiment, adequate relief of BD symptoms comprises an affirmative response (e.g., yes) from a subject if asked a weather they have had adequate relief of bloating.

In one embodiment, bloating symptoms comprise one or more of the symptoms of abdominal fullness, bloating, gas, or swelling.

In one embodiment, a BD comprises one or more of irritable bowel syndrome (IBS), uncontrolled diarrhea-associated Irritable Bowel Syndrome (dIBS), Crohn's disease, traveler's diarrhea, ulcerative colitis, enteritis, small intestinal bacterial overgrowth, chronic pancreatitis, pancreatic insufficiency, colitis, diverticular disease, hepatic encephalopathy, and/or or pouchitis.

In one embodiment, a BD may also comprise one or more of fibromyalgia (FM), chronic fatigue syndrome (CFS), depression, attention deficit/hyperactivity disorder (ADHD), multiple sclerosis (MS), and/or systemic lupus erythematosus (SLE).

In one aspect, presented herein are methods of treating bowel disease (BD) in males comprising, administering a therapeutically effective amount of rifaximin to a male in need thereof.

In one aspect, presented herein are methods of treating bowel disease (BD) in females comprising, administering a therapeutically effective amount of rifaximin to a female in need thereof.

In one embodiment, the methods further comprise determining the gender of a subject and administering the therapeutically effective amount to a male subject.

In one embodiment, the methods further comprise determining the gender of a subject and administering the therapeutically effective amount to a female subject.

In one embodiment, the methods further comprise determining symptom relief in a male subject and administering a second course of rifaximin treatment if symptoms remain unresolved.

In one aspect, presented herein are methods of treating bloating due to BD in males comprising administering a therapeutically effective amount of rifaximin to a male in need thereof.

In one aspect, presented herein are methods of treating BD in older subjects comprising administering a therapeutically effective amount of rifaximin to an older subject in need thereof, determining symptom relief in the older subject and administering a second course of rifaximin treatment if symptoms were unresolved. As used herein, an older subject, refers for example to a subject greater than 65 years of age, a subject about 50 years of age or older, a subject about 55 years of age or older, a subject about 60 years of age or older, or a subject about 70 years of age or older. A "long duration of disease," as used herein refers, for example, to a subject suffering from the disease for about 4 to about 10 or more years, or to a subject suffering from the disease from about 5 years to about 10 years, or to a subject suffering from the disease from about 5 years to about 20 years or greater.

In one aspect, presented herein are methods of predicting response to rifaximin treatment for BD comprising: assessing a subject suffering from BD and administering a therapeutically effective amount of rifaximin to one or more of a subject determined to be old, with long duration of BD, men or those having a baseline severity of mild to moderate.

In one aspect, presented herein are methods of treating BD in older subjects comprising administering a therapeutically effective amount of rifaximin to an older subject in need thereof. As used herein, an older subject, refers for example to a subject 65 years of age or older.

In one embodiment, the method further comprises determining, based on clinical data, weather a subject will have a positive response to treatment. In one embodiment, the determination is made based on one or more of a subject's age, a subject's duration of BD, gender, or baseline severity of BD. In one embodiment, the clinical data is presented in a label on a pharmaceutical product.

In one embodiment, the method further comprises determining, based on clinical data, weather a subject will have a positive response to treatment. In one embodiment, the determination is made based on one or more of a subject's age, race or gender. In one embodiment, the clinical data is presented in a label on a pharmaceutical product.

In one embodiment, if a subject is male, there is a prediction of response.

In one embodiment, if a subject is older, there is a prediction of response.

In one embodiment, if a subject has had a long duration of disease, there is a prediction of response.

In one embodiment, the method further comprises determining, based on clinical data, weather a subject will have a positive response to treatment. In one embodiment, the determination is made based on one or more of a subject's age, race or gender. In one embodiment, the clinical data is presented in a label on a pharmaceutical product.

In one embodiment, baseline severity determination comprises a 7-point Lickert scale.

In one embodiment, the methods further comprise notifying the subject of a likelihood of response.

In one embodiment, a subject's likelihood of response increases with age and with length of duration of BD.

In one embodiment, the therapeutically effective amount comprises from between about 100 mg and about 6000 mg; 550 mg TID; 550 mg BID; 600 mg TID; 600 mg BID; or 1650 mg.

In one aspect, presented herein are methods of treating BD, comprising: providing a container comprising a rifamycin class antibiotic, wherein the container comprises printed labeling which describes a durability of antibiotic response and suggests selecting subject's who respond to treatment have a durability of response after removal from treatment; and administering rifaximin from the container to the subject.

In one aspect, presented herein are methods of treating BD, comprising: providing a container comprising rifaximin, wherein the container comprises printed labeling which describes the administration instructions; and administering rifaximin from the container to the subject to treat BD. In one embodiment, the rifamycin class antibiotic comprises rifaximin.

In one aspect, presented herein are kits for treating BD comprising a container comprising a rifamycin class antibiotic and a label which describes that administration of a therapeutically effective amount of the antibiotic results in a durability of response in a subject that responds to the treatment. In one embodiment, the rifamycin class antibiotic is rifaximin.

In one embodiment, the label describes adverse events comprising one or more of infections and infestations, gastrointestinal disorders, nervous system disorders, and musculoskeletal and connective tissue disorders.

In one embodiment, the label describes a length of treatment with the rifamycin class antibiotic, whereby a subject is selected as responding to treatment if a healthcare professional prescribes the rifamycin class antibiotic according to the label instructions.

In one embodiment, the label describes a length of treatment with rifaximin, whereby a subject is selected as responding to treatment if a healthcare professional prescribes the rifamycin class antibiotic according to the label instructions.

In one embodiment, the label describes a length of treatment with the rifamycin class antibiotic, whereby a subject is removed from treatment if a healthcare professional prescribes the rifamycin class antibiotic according to the label instructions.

In one embodiment, the label describes a length of treatment with rifaximin, whereby a subject is removed from treatment if a healthcare professional prescribes the rifamycin class antibiotic according to the label instructions.

In one aspect, the rifamycin class antibiotic comprises one or more of rifaximin or a Form α, Form β, Form γ, Form δ, Form ε, Form ζ, Form η, Form α-dry, Form ι, Form β-1, Form β-2, Form ε-dry, mesylate Form or amorphous Forms of rifaximin and a pharmaceutically acceptable carrier. The rifaximin may be formulated as a pharmaceutical composition. In one embodiment, the rifamycin class antibiotic comprises rifaximin.

In one embodiment, the pharmaceutical composition further comprises excipients.

According to another embodiment, the excipients comprise one or more of a diluting agent, binding agent, lubricating agent, disintegrating agent, coloring agent, flavorings agent or sweetening agent.

In another embodiment, the composition is formulated for selected coated and uncoated tablets, hard and soft gelatin capsules, sugar-coated pills, lozenges, wafer sheets, pellets and powders in sealed packet. In one embodiment, the composition is formulated for topical use.

According to another embodiment, the bowel related disorder is one or more of irritable bowel syndrome (IBS), diarrhea-predominant Irritable Bowel Syndrome (dIBS), Crohn's disease, traveler's diarrhea, ulcerative colitis, enteritis, small intestinal bacterial overgrowth, chronic pancreatitis, pancreatic insufficiency, colitis, diverticular disease, hepatic encephalopathy, and/or or pouchitis.

According to one aspect, provided herein are methods of improving QOL measures in a BD subject comprising administering rifaximin.

According to one aspect, provided herein are methods of improving QOL measures in a BD subjects comprising administering a rifamycin class antibiotic.

In one embodiment, rifaximin is administered for 14 days.

In one embodiment, one or more of quality of life (QOL) measures comprising dysphoria, body image, health worry, social reaction, and relationship are improved upon administration of rifaximin.

In one embodiment, selecting comprises following dosing instructions on a package insert of a pharmaceutical product.

In one embodiment, the package insert instructs to administer the rifamycin class antibiotic for 14 days.

In one embodiment, removing comprises instructing a subject by following dosing instructions on a package insert of a pharmaceutical product.

In one embodiment, the package insert instructs to administer the rifamycin class antibiotic for 14 days.

In one embodiment, the package insert instructs to administer the rifaximin for 14 days.

In one embodiment, the product comprises 550 mg of rifaximin labeled for treatment of irritable bowel syndrome.

In one embodiment, the product comprises 550 mg of rifaximin labeled for treatment of hepatic encephalopathy.

In one embodiment, the product comprises 600 mg of rifaximin labeled for treatment of irritable bowel syndrome.

In one embodiment, the product comprises 600 mg of rifaximin labeled for treatment of hepatic encephalopathy.

In one embodiment, the product comprises 550 mg of rifaximin labeled for treatment of one or more of irritable bowel syndrome, Travelers' diarrhea or hepatic encephalopathy.

In one embodiment, the product comprises 550 mg of rifaximin.

In one embodiment, the product comprises 600 mg of rifaximin.

In one embodiment, the product comprises 200 mg of rifaximin.

In one embodiment, the product comprises 400 mg of rifaximin.

In one embodiment, the product comprises 400 mg of rifaximin BID.

In one embodiment, the product comprises 400 mg of rifaximin TID.

In one embodiment, the method further comprises determining risk of BD in a subject prior to administration of the rifamycin class antibiotic by genetically profiling the subject risk of BD and selecting to administer a rifamycin class antibiotic to an at risk subject.

In one embodiment, determining risk comprises determining polymorphisms at one or more of Nod2, CFTR, CARD15, rs6822844, rs2305767, rs6822844, 8q24 region; Marker:rs6983267, LOC727677, IL23R(1), NKX2-3, 5p13 region, PTPN2, MST1, IRGM, IL23R(2), or 10q21 region.

Provided herein, according to one aspect are methods of providing acute treatment for symptomatic diarrhea-predominant Irritable Bowel Syndrome (dIBS) comprising: administering 1650 mg/day of rifaximin for 14 days to a subject in need thereof, wherein removing the subject from treatment after the 14 days results in a durability of response.

In one embodiment, the 1650 mg is administered as 550 mg three times a day.

Provided herein, according to one aspect are methods of providing acute treatment for uncontrolled diarrhea-predominant Irritable Bowel Syndrome (dIBS) comprising: administering 550 mg rifaximin two or three times a day for two weeks to a subject in need thereof, wherein removing the subject from treatment after the two weeks results in a durability of response.

In one embodiment, the treatment provides symptomatic relief of dIBS.

In one embodiment, a package insert of a pharmaceutical product warns of adverse events, including, for example, infections and infestations, gastrointestinal disorders, nervous system disorders, and musculoskeletal and connective tissue disorders.

In another embodiment, the invention provides methods of treating abdominal pain associated with Irritable Bowel Syndrome (IBS) by administering 550 mg of rifaximin TID to a subject in need thereof, thereby treating abdominal pain Irritable Bowel Syndrome (IBS).

In one embodiment, the IBS is diarrhea-predominant IBS. In another embodiment, the IBS is alternating-predominant IBS.

In one embodiment, treating IBS comprises treating an IBS symptom of pain.

In one embodiment, the IBS symptom of pain comprise abdominal pain.

In one embodiment, treating the IBS symptom of pain comprise adequate relief of pain.

In one embodiment, adequate relief of pain comprises a reduction of pain symptoms.

In one embodiment, the reduction in pain comprises a reduction from baseline symptoms.

In one embodiment, baseline symptoms are established prior to treatment.

In one embodiment, a subject having a diabetes history of longer than 20 years is predicted to respond to treatment with rifaximin.

Other embodiments of the invention are disclosed infra.

DETAILED DESCRIPTION

Figure 1:
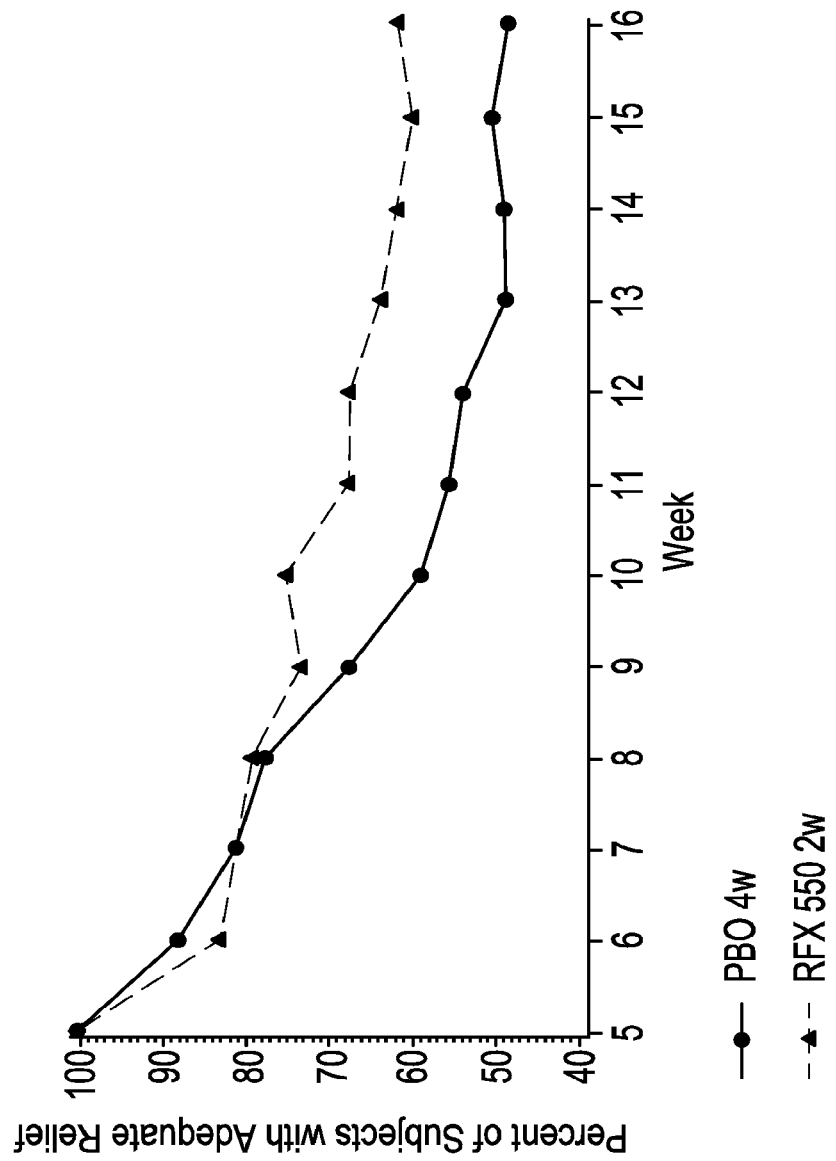
FIG. 1 shows a graph of continuous adequate relief of IBS symptoms during non-treatment follow-up.

Rifaximin (USAN, INN; see The Merck Index, XIII Ed., 8304, CAS No. 80621-81-4), (2S,16Z,18E,20S,21S,22R,23R,24R,25S,26S,27S,28E)-5,6,21,23,25 Pentahydroxy-27-methoxy-2,4,11,16,20,22,24,26-octamethyl-2,7-(epoxypentadeca-(1,11,13) trienimino) benzofuro (4,5-e) pyrido(1,2,-a) benzimidazole-1,15(2H)-dione,25-acetate), is a semi-synthetic antibiotic produced from rifamycin O. Rifaximin is a molecule belonging to the rifamycin class of antibiotics, e.g., a pyrido-imidazo rifamycin. Rifaximin exerts a broad antibacterial activity, for example, in the gastrointestinal tract against localized gastrointestinal bacteria that cause infectious diarrhea, irritable bowel syndrome, small intestinal bacterial overgrowth, Crohn's disease, and/or pancreatic insufficiency.

Rifaximin is also described in Italian Patent IT 1154655 and EP 0161534. EP patent 0161534 discloses a process for rifaximin production using rifamycin O as the starting material (The Merck Index, XIII Ed., 8301). U.S. Pat. No. 7,045,620 B1 discloses polymorphic forms of rifaximin, as do U.S. Ser. No. 11/658,702; U.S. Ser. No. 61/031,329; U.S. Ser. No. 12/119,622; U.S. Ser. No. 12/119,630; U.S. Ser. No. 12/119,612; U.S. Ser. No. 12/119,600; U.S. Ser. No. 11/873,841; Publication WO 2006/094662; and U.S. Ser. No. 12/393,012. The applications and patents referred to here are incorporated herein by reference in their entirety for all purposes.

A rifamycin class antibiotic is, for example, a compound having the structure of Formula I:

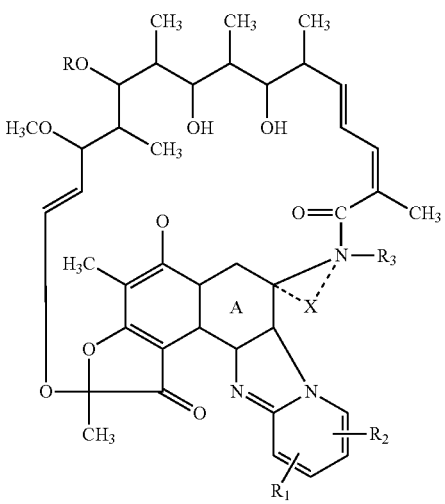

wherein A may be the structure $A_1$:

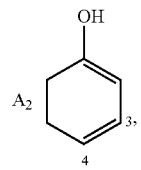

or the structure $A_2$

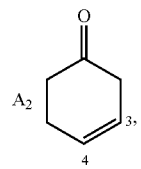

wherein, -x- is a covalent chemical bond or nil; R is hydrogen or acetyl; $R_1$ and $R_2$ independently represent hydrogen, $(C_{1-4})$ alkyl, benzyloxy, mono- and di-$(C_{1-3})$ alkylamino-$(C_{1-4})$ alkyl, $(C_{1-3})$alkoxy-$(C_{1-4})$alkyl, hydroxymethyl, hydroxy-$(C_{2-4})$-alkyl, nitro or $R_1$ and $R_2$ taken together with two consecutive carbon atoms of the pyridine nucleus form a benzene ring unsubstituted or substituted by one or two methyl or ethyl groups; $R_3$ is a hydrogen atom or nil; with the proviso that, when A is $A_1$, -x- is nil and $R_3$ is a hydrogen atom; with the further proviso that, when A is $A_2$, -x- is a covalent chemical bond and $R_3$ is nil.

Also described herein is a compound as defined above, wherein A is $A_1$ or $A_2$ as above indicated, -x- is a covalent chemical bond or nil, R is hydrogen or acetyl, $R_1$ and $R_2$ independently represent hydrogen, $(C_{1-4})$alkyl, benzyloxy, hydroxy-$(C_{2-4})$ alkyl, di-$(C_{1-3})$ alkylamino-$(C_{1-4})$ alkyl, nitro or $R_1$ and $R_2$ taken together with two consecutive carbon atoms of the pyridine nucleus form a benzene ring and $R_3$ is a hydrogen atom or nil; with the proviso that, when A is $A_1$, -x- is nil and $R_3$ is a hydrogen atom; with the further proviso that, when A is $A_2$, -x- is a covalent chemical bond and $R_3$ is nil.

Also described herein is a compound as defined above, wherein A is $A_1$ or $A_2$ as above indicated, -x- is a covalent chemical bond or nil, R is acetyl, $R_1$ and $R_2$ independently represent hydrogen, $(C_{1-4}$ alkyl or $R_1$ and $R_2$ taken together with two consecutive carbon atoms of the pyridine nucleus form a benzene ring and $R_3$ is a hydrogen atom or nil; with the proviso that, when A is $A_1$, -x- is nil and $R_3$ is a hydrogen atom; with the further proviso that, when A is $A_2$, -x- is a covalent chemical bond and $R_3$ is nil.

Also described herein is a compound as defined above, which is 4-deoxy-4'-methyl-pyrido[1',2'-1,2]imidazo [5,4-c] rifamycin SV. Also described herein is a compound as defined above, which is 4-deoxy-pyrido [1',2':1,2]imidazo [5,4-c] rifamycin SV.

Also described herein is a compound as defined above, wherein A is as described above, -x- is a covalent chemical bond or nil; R is hydrogen or acetyl; $R_1$ and $R_2$ independently represent hydrogen, $(C_{1-4})$ alkyl, benzyloxy, mono- and di-$(C_{1-3})$alkylamino$(C_{1-4})$alkyl, $(C_{1-3})$alkoxy-$(C_{1-4})$ alkyl, hydroxymethyl, hydroxy-$(C_{2-4})$-alkyl, nitro or $R_1$ and $R_2$ taken together with two consecutive carbon atoms of the pyridine nucleus form a benzene ring unsubstituted or substituted by one or two methyl or ethyl groups; $R_3$ is a hydrogen atom or nil; with the proviso that, when A is $A_1$, -x- is nil and $R_3$ is a hydrogen atom; with the further proviso that, when A is $A_2$, -x- is a covalent chemical bond and $R_3$ is nil.

Rifaximin is a compound having the structure of formula II:

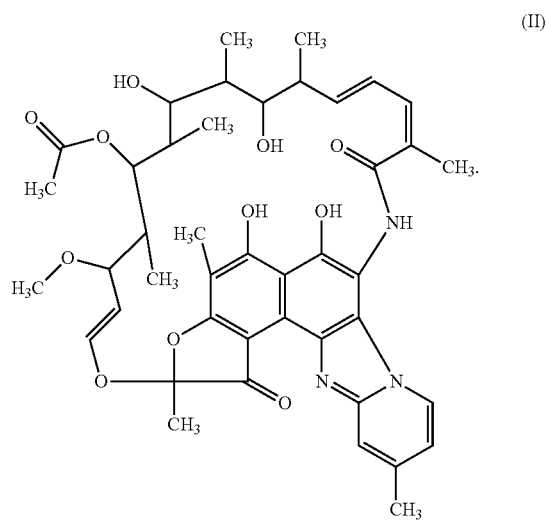 [SMILES: COC1/C=C/OC2(C)Oc3c(C)c(O)c4c(O)c(c5c(nc6cc(C)ccn65)c4c3C2=O)NC(=O)/C(C)=C\C=C\C(C)C(O)C(C)C(O)C(C)C(OC(C)=O)C1C]

(II)

In certain embodiments, the antibiotic comprises one or more of a rifamycin, aminoglycoside, amphenicol, ansamycin, β-Lactam, carbapenem, cephalosporin, cephamycin, monobactam, oxacephem, lincosamide, macrolide, polypeptide, tetracycline, or a 2,4-diaminopyrimidine class antibiotic. Exemplary antibiotics of these classes are listed below.

Without wishing to be bound by any particular scientific theories, rifaximin acts by binding to the beta-subunit of the bacterial deoxyribonucleic acid-dependent ribonucleic acid (RNA) polymerase, resulting in inhibition of bacterial RNA synthesis. It is active against numerous gram (+) and ( ) bacteria, both aerobic and anaerobic. In vitro data indicate rifaximin is active against species of Staphylococcus, Streptococcus, Enterococcus, and Enterobacteriaceae.

"Rifaximin", as used herein, includes solvates and polymorphous forms of the molecule, including, for example, Form α, Form β, Form γ Form δ, Form ε, Form ζ, Form η, Form α-dry, Form ι, Form β-1, Form β-2, Form ε-dry, mesylate Form or amorphous Forms of rifaximin. These forms are described in more detail, for example, in U.S. Ser. No. 11/873,841; U.S. Ser. No. 11/658,702; EP 05 004 635.2, filed 3 May 2005; U.S. Pat. No. 7,045,620; U.S. 61/031,329; G. C. Viscomi, et al., CrystEngComm, 2008, 10, 1074-1081 (April 2008), US Patent Publication 2010/0174064, US Patent Publication 2009/0234114; US Patent Publication 2009/0262012, US Patent Publication 2009/0130201, US Patent Publication 2009/0082558, US Patent Publication 2009/0028940, US Patent Publication 2005/0272754. Each of these references is hereby incorporated by reference in entirety.

Medicinal preparations may contain gastrointestinal specific antibiotics together with usual excipients, discussed infra.

"Polymorphs" or "polymorphic forms" as used herein, refer to the occurrence of different crystalline forms of a single compound in distinct hydrate status, e.g., a property of some compounds and complexes. Thus, polymorphs are distinct solids sharing the same molecular formula, yet each polymorph may have distinct physical properties. Therefore, a single compound may give rise to a variety of polymorphic forms where each form has different and distinct physical properties, such as solubility profiles, melting point temperatures, hygroscopicity, particle shape, density, flowability, compatibility and/or x-ray diffraction peaks. The solubility of each polymorph may vary, thus, identifying the existence of pharmaceutical polymorphs is essential for providing pharmaceuticals with predictable solubility profiles. It is desirable to investigate all solid state forms of a drug, including all polymorphic forms, and to determine the stability, dissolution and flow properties of each polymorphic form. Polymorphic forms of a compound can be distinguished in a laboratory by X-ray diffraction spectroscopy and by other methods such as, infrared spectrometry. For a general review of polymorphs and the pharmaceutical applications of polymorphs see G. M. Wall, Pharm Manuf. 3, 33 (1986); J. K. Haleblian and W. McCrone, J Pharm. Sci., 58, 911 (1969); and J. K. Haleblian, J. Pharm. Sci., 64, 1269 (1975), all of which are incorporated herein by reference. As used herein, the term polymorph is occasionally used as a general term in reference to the forms of rifaximin and include within the context, salt, hydrate, polymorph and amorphous forms of rifaximin disclosed herein. This use depends on context and will be clear to one of skill in the art. Exemplary polymorphic forms of rifaximin useful in the methods and kits of the invention are set forth in the published patent applications set forth above.

"GI specific antibiotic," and "GI antibiotic" as used herein include antibiotic known to have an effect on GI disease. For example, a rifamycin class antibiotic (e.g., rifaximin), neomycin, metronidazole, teicoplanin, ciprofloxacin, doxycycline, tetracycline, augmentin, cephalexin, penicillin, ampicillin, kanamycin, rifamycin, vancomycin, and combinations thereof are useful GI specific antibiotics. Even more preferable are GI specific antibiotics with low systemic absorption, for example, rifaximin. Low systemic absorption includes, for example, less than 10% absorption, less than 5% absorption, less than 1% absorption and less than 0.5% absorption. Low systemic absorption also includes, for example, from between about 0.01-1% absorption, from between about 0.05-1% absorption, from between about 0.1-1% absorption, from between about 1-10% absorption, or from between about 5-20% absorption.

"Ameliorate," "amelioration," "improvement" or the like refers to, for example, a detectable improvement or a detectable change consistent with improvement that occurs in a subject or in at least a minority of subjects, e.g., in at least about 2%, 5%, 10%, 15%, 20%, 25%, 30%, 40%, 50%, 60%, 70%, 75%, 80%, 85%, 90%, 95%, 98%, 100% or in a range between about any two of these values. Such improvement or change may be observed in treated subjects as compared to subjects not treated with rifaximin, where the untreated subjects have, or are subject to developing, the same or similar disease, condition, symptom or the like. Amelioration of a disease, condition, symptom or assay parameter may be determined subjectively or objectively, e.g., self assessment by a subject(s), by a clinician's assessment or by conducting an appropriate assay or measurement, including, e.g., a quality of life assessment, a slowed progression of a disease(s) or condition(s), a reduced severity of a disease(s) or condition(s), or a suitable assay(s) for the level or activity(ies) of a biomolecule(s), cell(s) or by detection of BD episodes in a subject. Amelioration may be transient, prolonged or permanent or it may be variable at relevant times during or after a GI specific antibiotic is administered to a subject or is used in an assay or other method described herein or a cited reference, e.g., within timeframes described infra, or about 1 hour after the administration or use of a GI specific antibiotic to about 7 days, 2 weeks, 28 days, or 1, 3, 6, 9 months or more after a subject(s) has received such treatment.

The "modulation" of, e.g., a symptom, level or biological activity of a molecule, or the like, refers, for example, that the symptom or activity, or the like is detectably increased or decreased. Such increase or decrease may be observed in treated subjects as compared to subjects not treated with a GI specific antibiotic, where the untreated subjects have, or are subject to developing, the same or similar disease, condition, symptom or the like. Such increases or decreases may be at least about 2%, 5%, 10%, 15%, 20%, 25%, 30%, 40%, 50%, 60%, 70%, 75%, 80%, 85%, 90%, 95%, 98%, 100%, 150%, 200%, 250%, 300%, 400%, 500%, 1000% or more or within any range between any two of these values. Modulation may be determined subjectively or objectively, e.g., by the subject's self assessment, by a clinician's assessment or by conducting an appropriate assay or measurement, including, e.g., quality of life assessments or suitable assays for the level or activity of molecules within a subject. Modulation may be transient, prolonged or permanent or it may be variable at relevant times during or after a GI specific antibiotic is administered to a subject or is used in an assay or other method described herein or a cited reference, e.g., within times descried infra, or about 1 hour of the administration or use of a GI specific antibiotic to about 2 weeks, 28 days, 3, 6, 9 months or more after a subject(s) has received a GI specific antibiotic.

The term "modulate" may also refer to increases or decreases in the activity of a cell in response to exposure to a GI specific antibiotic, e.g., the inhibition of proliferation and/or induction of differentiation of at least a sub-population of cells in an animal such that a desired end result is achieved, e.g., a therapeutic result of GI specific antibiotic used for treatment may increase or decrease over the course of a particular treatment.

The language "a prophylactically effective amount" of a compound refers to an amount of a compound of the invention of formula I, formula II, or otherwise described herein which is effective, upon single or multiple dose administration to the subject, in preventing or treating BD.

As used herein, "subject" includes organisms which are capable of suffering from a bowel disease or other disorder treatable by a rifamycin class antibiotic (e.g., rifaximin) or who could otherwise benefit from the administration of a rifamycin class antibiotic (e.g., rifaximin) as described herein, such as human and non-human animals. Preferred human animals include human subjects. The term "non-human animals" of the invention includes all vertebrates, e.g., mammals, e.g., rodents, e.g., mice, and non-mammals, such as non-human primates, e.g., sheep, dog, cow, chickens, amphibians, reptiles, etc. Susceptible to a bowel disorder is meant to include a subject at risk of developing a bowel disorder or a person who is in remission from a BD or a person who may relapse from a BD, e.g., a subject suffering from immune suppression, a subject that has been exposed to a bacterial infection, physicians, nurses, a subject traveling to remote areas known to harbor bacteria that cause travelers' diarrhea, a family history of BD, an aging person, a person with liver damage, a subject in IBS remission, a subject who has had HE episodes in the past, a person with mind HE, a subject with uncontrollable diarrhea, a subject with dIBS, etc.

The language "a prophylactically effective amount" of a compound refers to an amount of a compound of the invention of formula I, formula II, or otherwise described herein which is effective, upon single or multiple dose administration to the subject, in preventing or treating BD or IBS.

The term "administration" or "administering" includes routes of introducing a GI specific antibiotic to a subject to perform their intended function. Examples of routes of administration that may be used include injection, oral, inhalation, vaginal, rectal and transdermal. The pharmaceutical preparations may be given by forms suitable for each administration route. For example, these preparations are administered in tablets or capsule form, by injection, inhalation, eye lotion, eye drops, ointment, suppository, etc. administration by injection, infusion or inhalation; topical by lotion or ointment; and rectal by suppositories. Oral administration is preferred. The injection can be bolus or can be continuous infusion. Depending on the route of administration, a GI specific antibiotic can be coated with or disposed in a selected material to protect it from natural conditions that may detrimentally effect its ability to perform its intended function. A GI specific antibiotic can be administered alone, or in conjunction with either another agent or agents as described above or with a pharmaceutically-acceptable carrier, or both. A GI specific antibiotic can be administered prior to the administration of the other agent, simultaneously with the agent, or after the administration of the agent. Furthermore, a GI specific antibiotic can also be administered in a proform, which is converted into its active metabolite, or more active metabolite in vivo.

Administration "in combination with" one or more further therapeutic agents includes simultaneous (concurrent) and consecutive administration in any order.

As will be readily apparent to one skilled in the art, the useful in vivo dosage to be administered and the particular mode of administration will vary depending upon the age, weight and mammalian species treated, the particular compounds employed, and/or the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved.

The term "obtaining" as in "obtaining a GI specific antibiotic" is intended to include purchasing, synthesizing or otherwise acquiring a GI specific antibiotic.

The language "a prophylactically effective amount" of a compound refers to an amount of a GI specific antibiotic which is effective, upon single or multiple dose administration to the subject, in preventing or treating IBS.

The term "pharmaceutical agent composition" (or agent or drug) as used herein refers to a chemical compound, composition, agent or drug capable of inducing a desired therapeutic effect when properly administered to a patient. It does not necessarily require more than one type of ingredient.

As used herein, "durability of response" includes for example, adequate relief of symptoms after removal of treatment, continuous adequate relief of symptoms after removal of treatment, or response that is greater than or superior to placebo response. A response by a subject may be considered durable, for example, if they have a response to the rifamycin class antibiotic after removal from treatment. The duration of response, may be, for example, 2 days, 7 days, two weeks, 3 weeks, 4 weeks, 12 weeks, between about 1 week and about 24 weeks or longer. The response may be measured, for example using one or more of the methods outlined below, including, for example, a subject's subjective assessment of their symptoms or a healthcare provider's or caretaker's assessment of a subject's symptoms.

As used herein, "selecting subject's who respond," "selection of subject's who respond" or the like, include, for example, determining that a subject has responded to treatment based on a decrease of BD or IBS symptoms and/or following label instructions to administer a product (e.g., a rifamycin class antibiotic) for a certain period of time or the like. The determination or selection may be based on the label (e.g., package or package insert) instructions or on the a subject's subjective assessment of their symptoms or a healthcare provider's or caretaker's assessment of a subject's symptoms.

Methods of Treatment

Provided herein are methods of treating, preventing, or alleviating bowel related disorders comprising administering to a subject in need thereof an effective amount of rifaximin. Bowel related disorders (e.g., bowel diseases) include one or more of irritable bowel syndrome (IBS), alternating predominant IBS, diarrhea-predominant Irritable Bowel Syndrome (dIBS), Crohn disease, traveler's diarrhea, ulcerative colitis, enteritis, small intestinal bacterial overgrowth, chronic pancreatitis, pancreatic insufficiency, colitis, diverticular disease, hepatic encephalopathy, abdominal pain associated with IBS and/or pouchitis.

Table 1 below demonstrates differential response to to treatment with rifaximin based on gender, age and IBS type. Table 2 demonstrates response to the treatment is correlated with the duration of disease.

TABLE 1

| | Thresholds | Treatment effect (IBS Sx, Bloating) |
| --- | --- | --- |
| Gender | M versus. | 21%*, 13.6% |
| | F | 3.5%, 3.9% |

TABLE 1-continued

| | Thresholds | Treatment effect (IBS Sx, Bloating) |
| --- | --- | --- |
| Age | <65 versus. | 6.9%, 6.8% |
| | 65 | 19.1%, 3.2% |
| dIBS Type | dIBS only versus. | 6.3%, 4.5% |
| | aIBS | 31.4%*, 31.4% |

*p-value <0.05

TABLE 2

| | Thresholds | Treatment effect (IBS Sx, Bloating) |
| --- | --- | --- |
| Diabetes History | Y versus. | −12.7%, −5.6% |
| | N | 9.5%, 7.4% |
| Disease Duration: | 10 y | 1.8%, 2.8% |
| | 10-20 y | 20.1%, 11.7% |
| | >20 y | 46.6%*, 35.1% |

*p-value <0.05

It was surprisingly shown that a rifamycin class antibiotic (e.g., rifaximin) is particularly efficacious in males for the treatment of IBS.

Durability of Response

Embodiments of the invention relate to the discovery that the dosing regimes described herein of rifaximin results in a durability of response and amelioration of IBS symptoms in subjects in need thereof. One embodiment of the invention is a method of treating bowel disease (BD) with a durability of antibiotic response, by administering a therapeutically effective amount of a rifamycin class antibiotic to a subject in need thereof, selecting subjects who respond to treatment after being treated for between about 1 and about 24 weeks, and removing a responding subject from treatment wherein after removal of treatment there is a durability of response. The selecting may be by a healthcare professional, by self selection or by selection of one in a position to decide or discern symptoms or to diagnose a response to the antibiotic. Removal of treatment comprises, for example, ceasing to administer, ceasing to recommend administration of the antibiotic, and/or advising responding subjects to stop taking the antibiotic.

In one embodiment, the recommendation (e.g., selection) is made on a label of a pharmaceutical product, which indicates that the product should be administered for 14 days (e.g., two weeks). For example, a subject in need of treatment is administered rifaximin 550 mg TID for two weeks and instructed by a label. In one embodiment, the recommendation (e.g., selection) is made on a label of a pharmaceutical product, which indicates that the product should be administered for two weeks. For example, a subject in need of treatment is administered rifaximin 550 mg TID for two weeks as instructed by a label. In one embodiment, selecting is following dosing instructions on a package insert of a pharmaceutical product.

Also described herein are methods for maintenance of remission of bowel disease in a subject comprising administering a therapeutically effective amount of rifaximin for at least 25 weeks to a subject in need thereof.

Yet another aspect of this invention relates to a method of treating a subject (e.g., mammal, human, horse, dog, cat) with rifaximin who is in need thereof. Identifying a subject in need of such treatment can be in the judgment of a subject or a health care professional and can be subjective (e.g., opinion) or objective (e.g., measurable by a test or diagnostic method).

Rifaximin may be used in various treatment regimes. These regimes may vary depending upon the subject and the type of treatment.

Rifaximin may be administered, for example, twice a day, three times a day, or four times or more often as necessary per day. Rifaximin may be administered in doses, for example of from about between 25 mg BID to about 3000 mg TID. Another example is administering rifaximin from between about 4.0 g/day to about 7.25 g/day. The rifaximin may be administered, for example, in tablet form, powered form, liquid for or in capsules.

Subjects in need thereof include subjects having or that are susceptible to BD, are in remission from BD, males and/or older subjects with long duration of disease, as disclosed further below.

As used herein, a therapeutically effective amount means an amount effective, when administered to a human or non-human subject, to provide a therapeutic benefit such as an amelioration of symptoms, e.g., an amount effective to decrease the symptoms of IBS, or maintenance of remission of a IBS.

In certain embodiments, the rifaximin is administered to a subject from between about 1 week to about 6 weeks in duration, from between about 8 weeks to about 12 weeks in duration, or from between 1 day to about 7 days. The rifaximin may be administered from between about 1 day and about 1 year, or from 1 week to about 24 weeks. The rifaximin may be administered, for example, for the remainder of a subject's life. The rifaximin may be administered intermittently or continuously during the course of treatment. Length of treatment may vary depending on the type and length of disease and the proper length of treatment may be easily determined by one of skill in the art having the benefit of this disclosure.

For any of the embodiments, rifaximin may be administered, for example, once daily, twice daily, three times daily, or four times daily (or more often as necessary for a particular subject) to a subject. In some methods of the present invention comprise administering the rifaximin once daily to the subject because it may, for example, minimize the side effects and increase patient compliance. Also preferred, are twice and three times daily administration of rifaximin.

Dosages, according to certain preferred embodiments, range from between about 50 to about 6000 mg of rifaximin administered daily. For example, a dose of 550 mg may be administered to a subject twice daily. Other appropriate dosages for methods according to this invention may be determined by health care professionals or by the subject. The amount of rifaximin administered daily may be increased or decreased based on the weight, age, health, sex or medical condition of the subject. One of skill in the art would be able to determine the proper dose for a subject based on this disclosure.

According to certain embodiments, rifaximin may be administered in combination with other compounds, including for example, chemotherapeutic agents, anti-inflammatory agents, anti-pyretic agents radiosensitizing agents, radioprotective agents, urologic agents, anti-emetic agents, and/or anti-diarrheal agents. For example, cisplatin, carboplatin, docetaxel, paclitaxel, flurouracil, capecitabine, gemcitabine, irinotecan, topotecan, etoposide, mitomycin, gefitinib, vincristine, vinblastine, doxorubicin, cyclophosphamide, celecoxib, rofecoxib, valdecoxib, ibuprofen, naproxen, ketoprofen, dexamethasone, prednisone, prednisolone, hydrocortisone, acetaminophen, misonidazole, amifostine, tamsulosin, phenazopyridine, ondansetron, granisetron, alosetron, palonosetron, promethazine, prochlorperazine, trimethobenzamide, aprepitant, diphenoxylate with atropine, and/or loperamide.

Risk Selection Methods

The methods described herein may also further comprise genetically profiling for genetic risk of BD and selecting to treat an at risk subject. For example, an at-risk subject may be determined to be at risk of a bowel disease by genetic screening, family history, lifestyle, travel plans and the like. Genetic screening may, for example, be for genes and expression profiles or epigenetic modifiers shown to affect or predict bowel disease or susceptibility for bowel diseases. Mutations which may be screened for include mutations or polymorphisms in, for example, Nod2, CFTR, or CARD15. Nod2, a gene involved in the immune systems initial response to bacterial infection, significantly increases the risk of Crohn's disease. The CFTR protein resides in the surface of cells lining the digestive system, lungs and sweat glands. In normal cells, it acts as an ion channel that transports chloride into and out of cells. It also controls the regulation of other transport pathways regulating the passage of fluid and bicarbonate across cell membranes. DNA sequence variations (or mutations) alone do not explain CFTR-related gastrointestinal disease patterns; rather, epigenetic modifiers, or changes that leave the gene's sequence of DNA intact, influence CFTR expression.

For example, a subject may be typed for rs6822844 and/or rs2305767 to indicate risk of celiac disease. One study examined 778 individuals with celiac disease and 1,422 healthy controls. The authors found that each T at rs6822844 lowered subjects' risk of celiac disease by about 1.6 times. See Zhernakova A et al. (2007) "Novel association in chromosome 4q27 region with rheumatoid arthritis and confirmation of type 1 diabetes point to a general risk locus for autoimmune diseases." Am J Hum Genet 81(6):1284-8; and van Heel D A et al. (2007) "A genome-wide association study for celiac disease identifies risk variants in the region harboring IL2 and IL21." Nat Genet 39(7):827-9. Another study examined 463 individuals with celiac disease and 686 healthy controls. The authors found that people with a C at both copies had 2.3 times lower odds for celiac disease than those with the TT genotype. See Hunt K A et al. (2006) "Lack of association of MYO9B genetic variants with coeliac disease in a British cohort." Gut 55(7):969-72; Núñez C et al. (2006) "No evidence of association of the MYO9B polymorphisms with celiac disease in the Spanish population." Tissue Antigens 68(6):489-92; Cirillo G et al. (2007) "Do MYO9B genetic variants predispose to coeliac disease? An association study in a cohort of South Italian children." Dig Liver Dis 39(3):228-31; Cirillo G et al. (2007) "Do MYO9B genetic variants predispose to coeliac disease? An association study in a cohort of South Italian children." Dig Liver Dis 39(3):228-31; Cirillo G et al. (2007) "Do MYO9B genetic variants predispose to coeliac disease? An association study in a cohort of South Italian children." Dig Liver Dis 39(3):228-31.

For example, a subject may be typed for 8q24 region; Marker:rs6983267 to determine risk for colon cancer. This SNP occurs in a hypothetical gene called LOC727677. It has been suggested that the riskier version of this SNP is associated not only with an increased risk of colorectal cancer, but also with formation of the precancerous adenomatous polyps. The riskier version of this SNP has also been linked to prostate cancer in some studies, though more research is needed to confirm this association. See Haiman et al. (2007) "A common genetic risk factor colorectal and prostate cancer." Nat Genet 39(8):954-6; and Tomlinson et al. (2007) "A genome-wide association scan of tag SNPs identifies a susceptibility variant for colorectal cancer at 8q24.21." Nat Genet 39(8):984-988; and Zanke et al. (2007) "Genome-wide association scan identifies a colorectal cancer susceptibility locus on chromosome 8q24." Nat Genet 39(8):989-994.

For example, a subject may be typed for NOD2(1) SNP: rs2066844; NOD2(2) SNP: rs2066845; NOD2(3) SNP: rs2066847; IL23R(1) SNP: rs11209026; NKX2-3 SNP: rs11190140; 5p13 region SNP: rs17234657; PTPN2 SNP: rs1893217; MST1 SNP: rs3197999; IRGM SNP: rs7714584; IL23R(2) SNP: rs11805303; and/or 10q21 region SNP: rs10761659 to determine risk of Crohn's disease. See Hugot et al. (2001) "Association of NOD2 leucine-rich repeat variants with susceptibility to Crohn's disease." Nature 411(6837):599-603; Ogura et al. (2001) "A frameshift mutation in NOD2 associated with susceptibility to Crohn's disease." Nature 411(6837):603-6; Rioux et al. (2007) "Genome-wide association study identifies new susceptibility loci for Crohn disease and implicates autophagy in disease pathogenesis." Nat Genet 39(5):596-604; Libioulle et al. (2007) "Novel Crohn's disease locus identified by genome-wide association maps to a gene desert on 5p13.1 and modulates expression of PTGER4." PLoS Genet 3(4):e58; Hampe et al. (2007) "A genome-wide association scan of non-synonymous SNPs identifies a susceptibility variant for Crohn disease in ATG16L1." Nat Genet 39(2): 207-11; Duerr et al. (2006) "A genome-wide association study identifies IL23R as an inflammatory bowel disease gene." Science 314(5804):1461-1463; van Limbergen et al. (2007) "IL23R Arg381Gln is associated with childhood onset inflammatory bowel disease in Scotland." Gut 56(8): 1173-4; Wellcome Trust Case Control Consortium (2007) "Genome-wide association study of 14,000 cases of seven common diseases and 3,000 shared controls." Nature 447 (7145):661-78; Parkes et al. (2007) "Sequence variants in the autophagy gene IRGM and multiple other replicating loci contribute to Crohn's disease susceptibility." Nat Genet 39(7):830-2; Sheibanie et al. (2007) "The proinflammatory effect of prostaglandin E2 in experimental inflammatory bowel disease is mediated through the IL-23→IL-17 axis." J Immunol 178(12):8138-47; Simoncic et al. (2007) "The T cell protein tyrosine phosphatase is a negative regulator of janus family kinases 1 and 3." Curr Biol 12(6):446-53; You-Ten et al. (1997) "Impaired bone marrow microenvironment and immune function in T cell protein tyrosine phosphatase-deficient mice." J Exp Med 22(16):5662-8; Barrett et al. (2008) "Genome-wide association defines more than 30 distinct susceptibility loci for Crohn's disease." Nat Genet 40(8):955-62; Goyette er al. (2008) "Gene-centric association mapping of chromosome 3p implicates MST1 in IBD pathogenesis" Mucosal Immunology 1:131-138; Barrett et al. (2008). "Genome-wide association defines more than 30 distinct susceptibility loci for Crohn's disease." Nat Genet 40(8):955-62; McCarroll et al (2008) "Deletion polymorphism upstream of IRGM associated with altered IRGM expression and Crohn's disease." Nat Genet 40(9):1107-1112; and Singh et al. (2006) "Human IRGM induces autophagy to eliminate intracellular mycobacteria." Science 313(5792):1438-41.

Pharmaceutical Preparations

The invention also provides pharmaceutical compositions, comprising an effective amount of a rifamycin class antibiotic (e.g., rifaximin or a rifaximin polymorph) described herein and a pharmaceutically acceptable carrier. In a further embodiment, the effective amount is effective to treat a bacterial infection, e.g., small intestinal bacterial overgrowth, Crohn's disease, hepatic encephalopathy, antibiotic associated colitis, and/or diverticular disease.

For examples of the use of rifaximin and formulations thereof to treat Travelers' diarrhea, see Infante R M, Ericsson C D, Zhi-Dong J, Ke S, Steffen R, Riopel L, Sack D A, DuPont, H L. Enteroaggregative *Escherichia coli* Diarrhea in Travelers: Response to Rifaximin Therapy. Clinical Gastroenterology and Hepatology. 2004; 2:135-138; and Steffen R, M.D., Sack D A, M.D., Riopel L, Ph.D., Zhi-Dong J, Ph.D., Sturchler M, M.D., Ericsson C D, M.D., Lowe B, M. Phil., Waiyaki P, Ph.D., White M, Ph.D., DuPont H L, M.D. Therapy of Travelers' Diarrhea With Rifaximin on Various Continents. The American Journal of Gastroenterology. May 2003, Volume 98, Number 5, all of which are incorporated herein by reference in their entirety.

One embodiment pharmaceutical compositions comprising rifaximin or any polymorphic form thereof and a pharmaceutically acceptable carrier. That is, formulations may contain only one polymorph or may contain a mixture of more than one polymorph. Polymorph, in this context, refers to any physical form, hydrate, acid, salt or the like of rifaximin. Mixtures may be selected, for example on the basis of desired amounts of systemic adsorption, dissolution profile, desired location in the digestive tract to be treated, and the like. The pharmaceutical composition further comprises excipients, for example, one or more of a diluting agent, binding agent, lubricating agent, disintegrating agent, coloring agent, flavoring agent or sweetening agent. Compositions may be formulated for selected coated and uncoated tablets, hard and soft gelatin capsules, sugar-coated pills, lozenges, wafer sheets, pellets and powders in sealed packet. For example, compositions may be formulated for topical use, for example, ointments, pomades, creams, gels and lotions.

In an embodiment, the rifamycin class antibiotic (e.g., rifaximin) is administered to the subject using a pharmaceutically-acceptable formulation, e.g., a pharmaceutically-acceptable formulation that provides sustained delivery of the rifamycin class antibiotic (e.g., rifaximin) to a subject for at least 12 hours, 24 hours, 36 hours, 48 hours, one week, two weeks, three weeks, or four weeks after the pharmaceutically-acceptable formulation is administered to the subject.

In certain embodiments, these pharmaceutical compositions are suitable for topical or oral administration to a subject. In other embodiments, as described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "pharmaceutically acceptable" refers to those rifamycin class antibiotic (e.g., rifaximin) described herein, compositions containing such compounds, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" includes pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions. Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Compositions containing a rifamycin class antibiotic (e.g., rifaximin) include those suitable for oral, nasal, topical (including buccal and sublingual), rectal, vaginal, aerosol and/or parenteral administration. The compositions may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1% to about 99% of active ingredient, preferably from about 5% to about 70%, most preferably from about 10% to about 30%.

Liquid dosage forms for oral or rectal administration of the rifamycin class antibiotic (e.g., rifaximin) include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

In addition to inert diluents, the oral compositions can include adjuvants such as wetting agents, emulsifying and suspending agents, sweetening, flavoring, coloring, perfuming and preservative agents.

Suspensions, in addition to the active rifamycin class antibiotic (e.g., rifaximin) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions of the invention for rectal or vaginal administration may be presented as a suppository, which may be prepared by mixing one or more rifamycin class antibiotic (e.g., rifaximin) with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent. Compositions which are suitable for vaginal administration can include pessaries, tampons, creams, gels, pastes, foams or spray formulations containing such carriers as are known in the art to be appropriate.

Dosage forms for the topical or transdermal administration of a rifamycin class antibiotic (e.g., rifaximin) can include powders, sprays, ointments, pastes, creams, lotions, gels, solutions, patches and inhalants. The active rifamycin class antibiotic (e.g., rifaximin) may be mixed under sterile conditions with a pharmaceutically-acceptable carrier, and with any preservatives, buffers, or propellants which may be required.

The ointments, pastes, creams and gels may contain, in addition to rifamycin class antibiotic (e.g., rifaximin), excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a rifamycin class antibiotic (e.g., rifaximin), excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane. The rifamycin class antibiotic (e.g., rifaximin) can be alternatively administered by aerosol. This is accomplished, for example, by preparing an aqueous aerosol, liposomal preparation or solid particles containing the compound. A non-aqueous (e.g., fluorocarbon propellant) suspension could be used. Sonic nebulizers are preferred because they minimize exposing the agent to shear, which can result in degradation of the compound.

Examples of suitable aqueous and non-aqueous carriers which may be employed in the pharmaceutical compositions can include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, to prolong the effect of a drug, it is desirable to alter the absorption of the drug. This may be accomplished by the use of a liquid suspension of crystalline, salt oramorphous material having poor water solubility. The rate of absorption of the drug may then depend on its rate of dissolution which, in turn, may depend on crystal size and crystalline form. Alternatively, delayed absorption of a drug form is accomplished by dissolving or suspending the drug in an oil vehicle. When the rifamycin class antibiotic (e.g., rifaximin) are administered as pharmaceuticals, to humans and animals, they can be given per se or as a pharmaceutical composition containing, for example, 0.1 to 99.5% (more preferably, 0.5 to 90%) of active ingredient in combination with a pharmaceutically-acceptable carrier.

Regardless of the route of administration selected, the rifamycin class antibiotic (e.g., rifaximin), which may be used in a suitable hydrated form, and/or the pharmaceutical compositions of the present invention, are formulated into pharmaceutically-acceptable dosage forms by conventional methods known to those of skill in the art.

Actual dosage levels and time course of administration of the active ingredients in the pharmaceutical compositions of the invention may be varied so as to obtain an amount of the active ingredient which is effective to achieve the desired therapeutic response for a particular patient, composition, and mode of administration, without being toxic to the patient. An exemplary dose range is from 25 to 3000 mg per day.

In combination therapy treatment, both the compounds of this invention and the other drug agent(s) are administered to mammals (e.g., humans, male or female) by conventional methods. The agents may be administered in a single dosage form or in separate dosage forms. Effective amounts of the other therapeutic agents are well known to those skilled in the art. However, it is well within the skilled artisan's purview to determine the other therapeutic agent's optimal effective-amount range. In one embodiment of the invention in which another therapeutic agent is administered to an animal, the effective amount of the compound of this invention is less than its effective amount in case the other therapeutic agent is not administered. In another embodiment, the effective amount of the conventional agent is less than its effective amount in case the compound of this invention is not administered. In this way, undesired side effects associated with high doses of either agent may be minimized. Other potential advantages (including without limitation improved dosing regimens and/or reduced drug cost) will be apparent to those skilled in the art.

In various embodiments, the therapies (e.g., prophylactic or therapeutic agents) are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In preferred embodiments, two or more therapies are administered within the same patient's visit.

In certain embodiments, one or more of the rifamycin class antibiotic (e.g., rifaximin) and one or more other therapies (e.g., prophylactic or therapeutic agents) are cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time, optionally, followed by the administration of a third therapy (e.g., prophylactic or therapeutic agent) for a period of time and so forth, and repeating this sequential administration, i.e., the cycle in order to reduce the development of resistance to one of the therapies, to avoid or reduce the side effects of one of the therapies, and/or to improve the efficacy of the therapies.

In certain embodiments, the administration of the same compounds may be repeated and the administrations may be separated by at least about 1 day, 2 days, 3 days, 5 days, 10 days, 15 days, 30 days, 45 days, 3 weeks, 4 weeks, 5 weeks, 6 weeks, 12 weeks, 2 months, 75 days, 3 months, or at least 6 months. In other embodiments, the administration of the same therapy (e.g., prophylactic or therapeutic agent) other than a rifamycin class antibiotic (e.g., rifaximin) may be repeated and the administration may be separated by at least at least 1 day, 2 days, 3 days, 5 days, 10 days, 15 days, 30 days, 45 days, 2 months, 75 days, 3 months, or at least 6 months. In one embodiment, a label on a rifamycin class antibiotic may instruct, for example, do not repeat more often than every 6 weeks. In another embodiment, a label on a rifamycin class antibiotic may instruct, for example, do not repeat more often than every 3 weeks. In another embodiment, a label on a rifamycin class antibiotic may instruct, for example, do not repeat more often than every 3-12 weeks. Included within ranges given herein for dosage or administration are any value within the range.

In certain embodiments, retreatment is efficacious in combination with the methods disclosed herein. See for example, Rifaximin versus Other Antibiotics in the Primary Treatment and Retreatment of Bacterial Overgrowth in IBS, Janet Yang, Hyo-Rang Lee, Kimberly Low, Soumya Chatterjee, and Mark Pimentel, Dig Dis Sci (2008) 53:169-174. For example, methods as described herein may further comprise determining symptom relief in a subject and administering a second course of rifaximin treatment if symptoms remain unresolved. Methods may also further comprise, for example, determining the gender of a subject and administering the therapeutically effective amount to a male subject.

Certain indications may require longer treatment times. For example, travelers' diarrhea treatment may only last from between about 12 hours to about 72 hours, while a treatment for Crohn's disease may be from between about 1 day to about 3 months and a treatment for hepatic encephalopathy may be from between 1 day and 12 months. For example, HE may require chronic therapy for the remainder of a subject's life. Crohn's disease subjects may also require chronic therapy.

Kits

Kits are also provided herein, for example, kits for treating a bowel disorder in a subject treating bowel disease (BD) with a durability of antibiotic response; methods of treating bowel disease (BD) in females methods of treating bowel disease (BD) in males; methods of treating bloating due to BD in males; methods of treating bloating due to BD; methods of treating non-white subjects having BD; and/or methods of treating BD in older subjects; methods of treating BD in older subjects with long duration of disease; and/or methods of predicting response to rifaximin treatment for BD. The kits may contain, for example, a polymorph or amorphous form of rifaximin and instructions for use. The instructions for use may contain prescribing information, dosage information, storage information, and the like.

In one embodiment, the label describes adverse events comprising one or more of infections and infestations, gastrointestinal disorders, nervous system disorders, and musculoskeletal and connective tissue disorders.

In one embodiment, the label describes a length of treatment with the rifamycin class antibiotic, whereby a subject is selected as responding to treatment if a healthcare professional prescribes the rifamycin class antibiotic according to the label instructions.

In one embodiment, the label describes a length of treatment with the rifamycin class antibiotic, whereby a subject is removed from treatment if a healthcare professional prescribes the rifamycin class antibiotic according to the label instructions.

Label instructions, include, for example, instructions to take the rifamycin class antibiotic for 14 days for the treatment of IBS. The instructions could also read, for example, take for 1650 mg/day of rifaximin for 14 days for acute treatment of Irritable Bowel Syndrome (IBS).

Label instructions may also include instructions that a higher percentage of non-white subjects, female subjects and subjects 65 years of age or older have an adequate relief of IBS symptoms an/or adequate relief of IBS symptom of bloating.

Packaged compositions are also provided, and may comprise a therapeutically effective amount of one or more of a one or more of an amorphous form, Form α, Form β, Form γ, Form δ, Form ε, Form ζ, or Form η polymorph of rifaximin of rifaximin and a pharmaceutically acceptable carrier or diluent, wherein the composition is formulated for treating a subject suffering from or susceptible to a bowel disorder, and packaged with instructions to treat a subject suffering from or susceptible to a bowel disorder.

EXAMPLES

It should be appreciated that the invention should not be construed to be limited to the example, which is now described; rather, the invention should be construed to include any and all applications provided herein and all equivalent variations within the skill of the ordinary artisan.

Example 1

This example relates to a study of rifaximin in subjects with dIBS. Subjects received daily one of BID doses of placebo, rifaximin 275 mg, 550 mg, or 1100 mg for 14 days. A fifth group of subjects received rifaximin 550 mg BID for a period of 28 days. There were two measures of efficacy assessed. Subjects were questioned on the relief of overall IBS symptoms and bloating. Adequate relief of IBS related symptoms (SGA) and IBS-related bloating (IBS-B) were assessed, and a dose of 550 mg BID for 2 weeks demonstrated statistically significant relief. The analyses defined success as a "yes" response to questions regarding adequate relief.

Predictors of response analyses showed that the response was similar across some subgroups however, there were differences. Analyses on predictors of response demonstrated that age (older subjects and those with a longer IBS duration); sex (males) and baseline severity (mild to moderate symptoms) were predictors of response. All subpopulations in the study responded to therapy. Baseline severity was determined using 7-point Lickert scales during screening for Abdominal Pain/Discomfort and Bloating, and the number, type (normal, hard, loose) and urgency of bowel movements.

Duration of effect was assessed in a follow-up period. Subjects that responded in the 4 week treatment period were followed for an additional 3 months. The subjects in the placebo group had a greater rate of decline in response than the 550 mg BID 2 week group, demonstrating that subjects treated with rifaximin had a better chance of maintaining symptom relief than their placebo treated counterparts.

Percentage of Subjects with Adequate Relief of IBS and Bloating Symptoms

Figure 4:
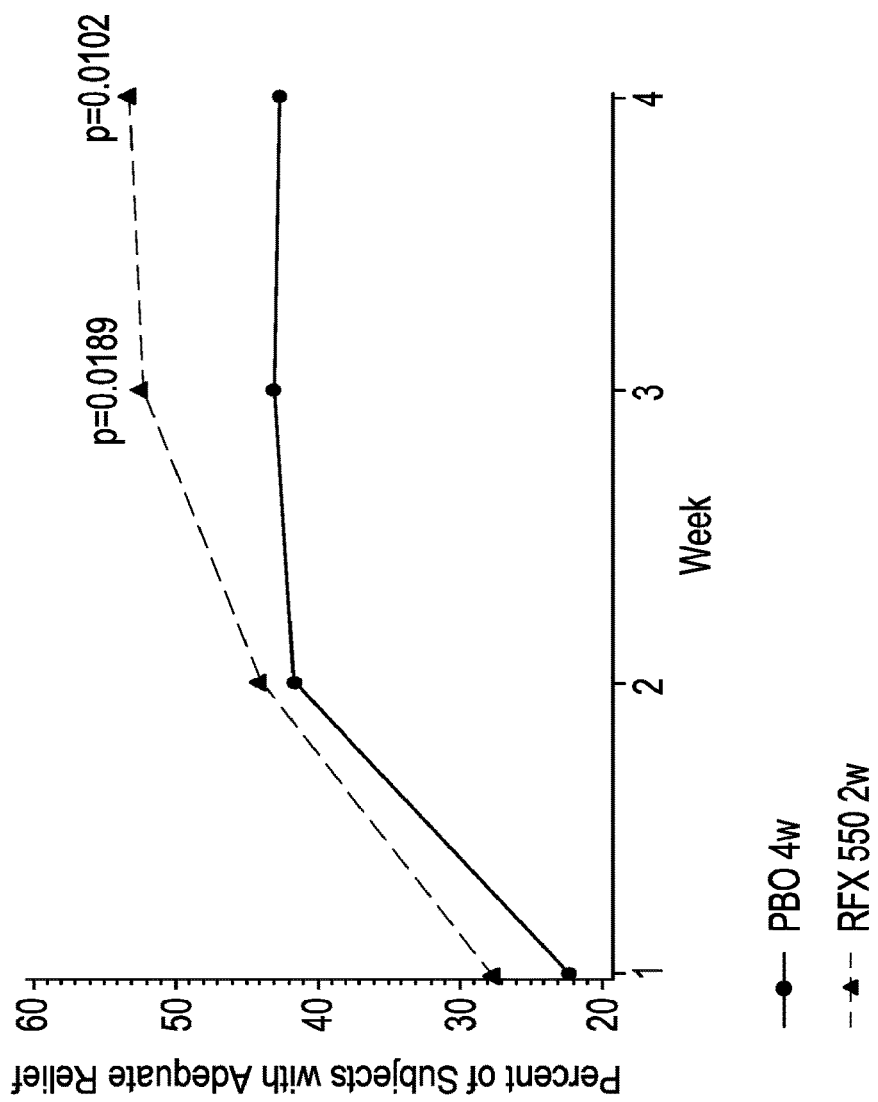
FIG. 4 shows graphical results of adequate relief of IBS symptoms.
Figure 5:
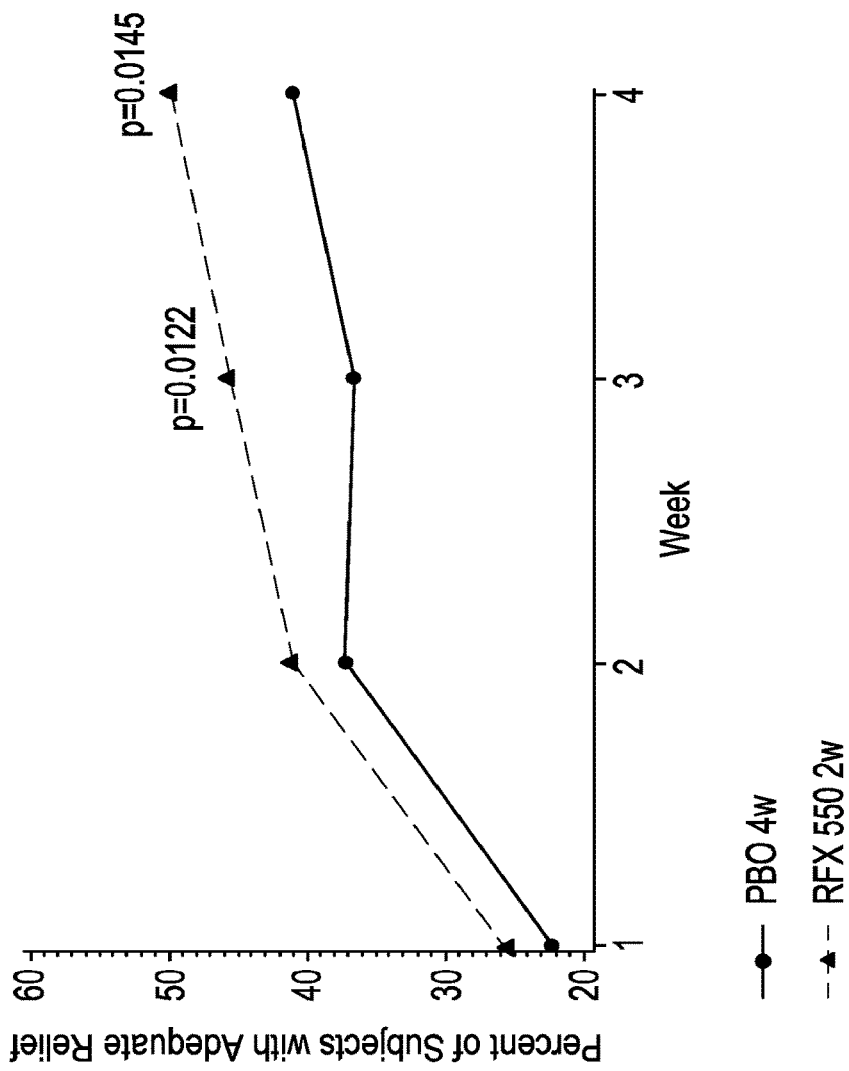
FIG. 5 shows results of adequate relief of bloating symptoms.
Figure 6:
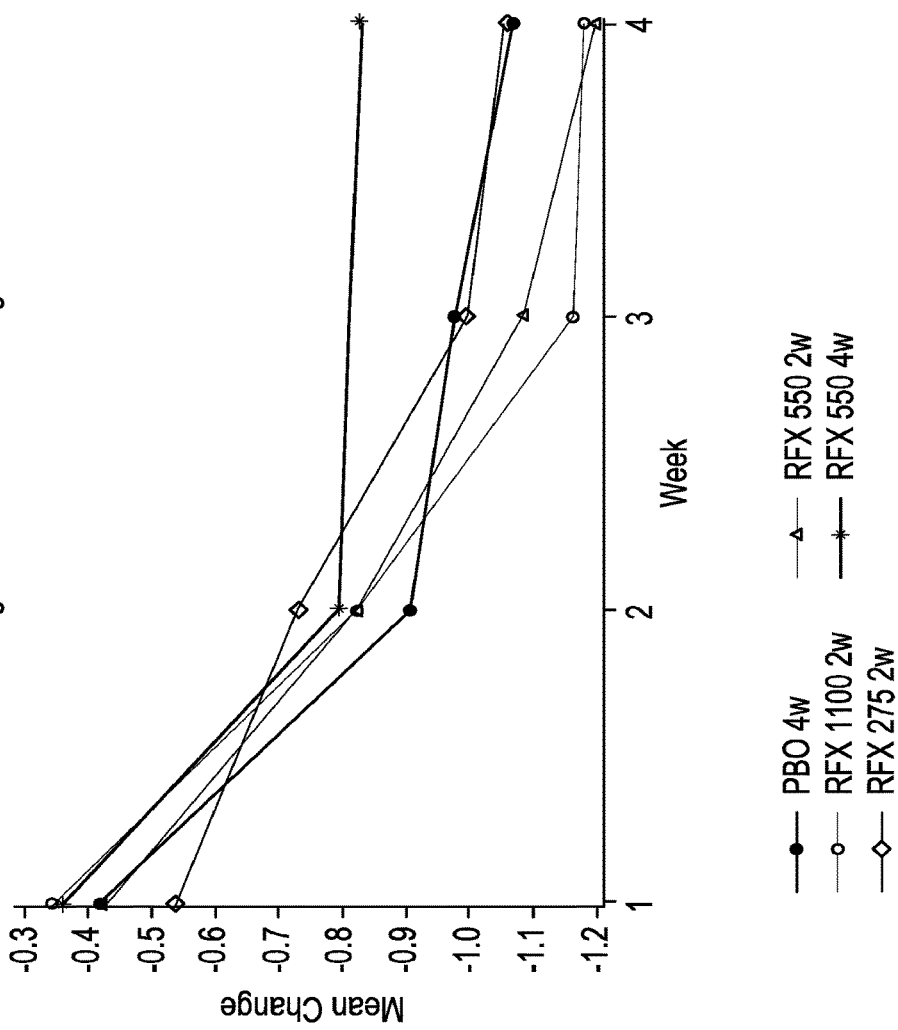
FIG. 6 shows results of change from baseline in bloating symptoms after treatment with rifaximin.
Figure 7:
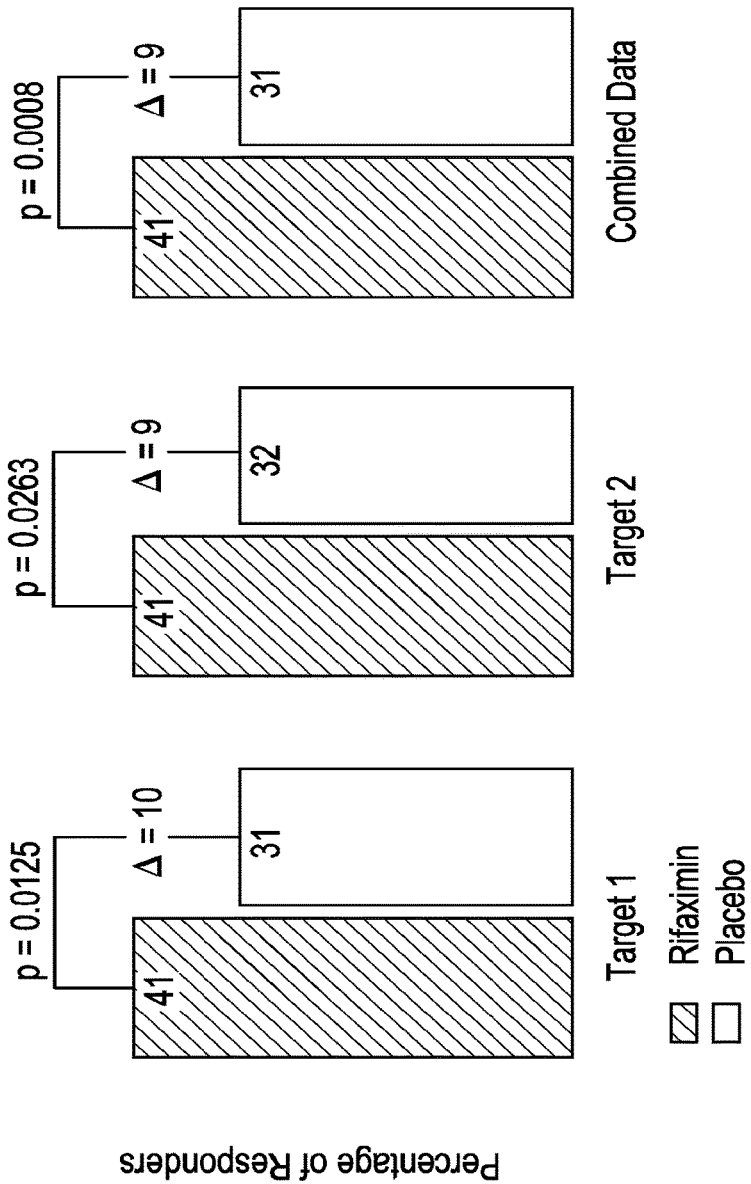
FIG. 7 shows an analysis of IBS weeks 3 through 6.
Figure 8:
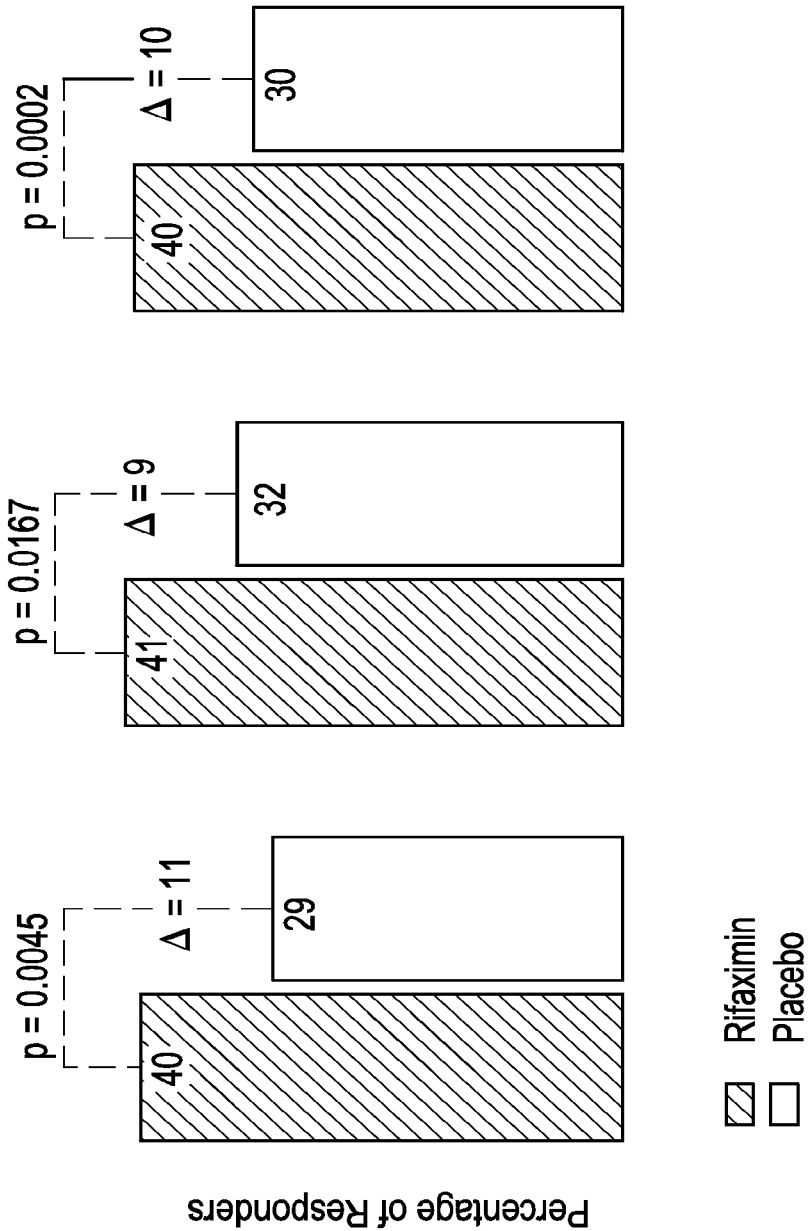
FIG. 8 shows IBS bloating data for weeks 3 through 6.
Figure 9:
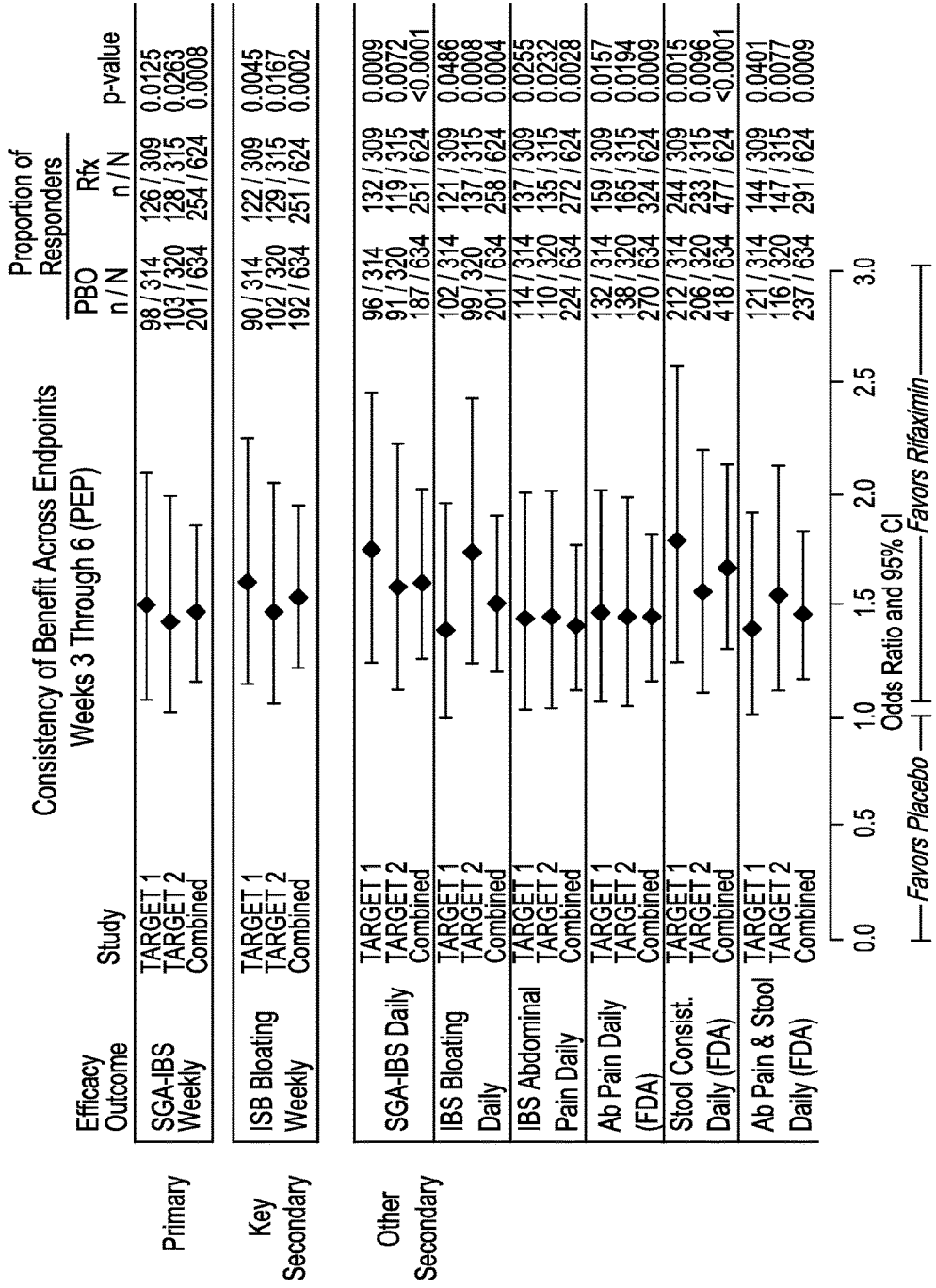
FIG. 9 shows IBS consistency data for weeks 3 through 6.
Figure 10:
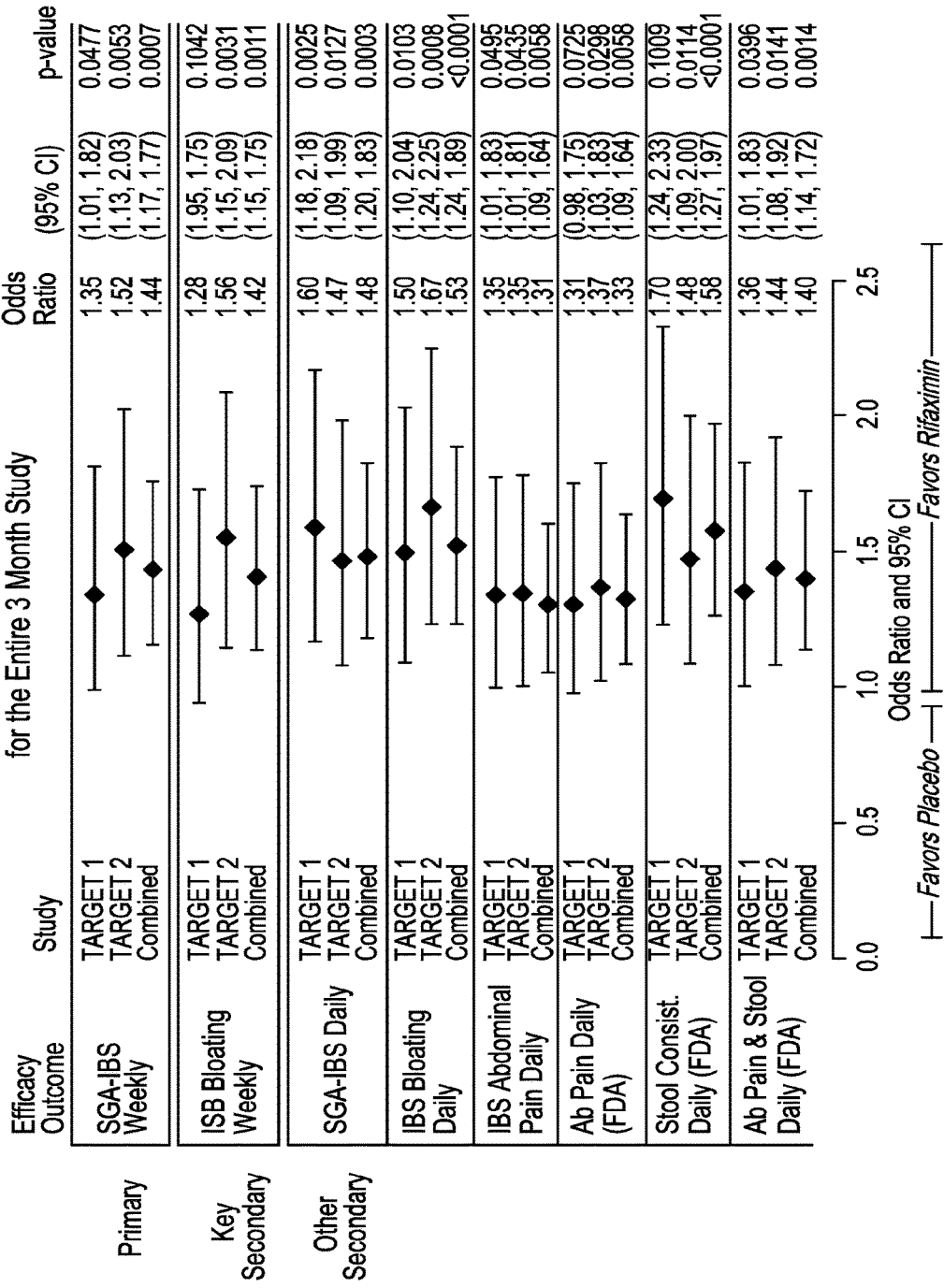
FIG. 10 shows IBS data for the entire 3 month study.
Figure 11:
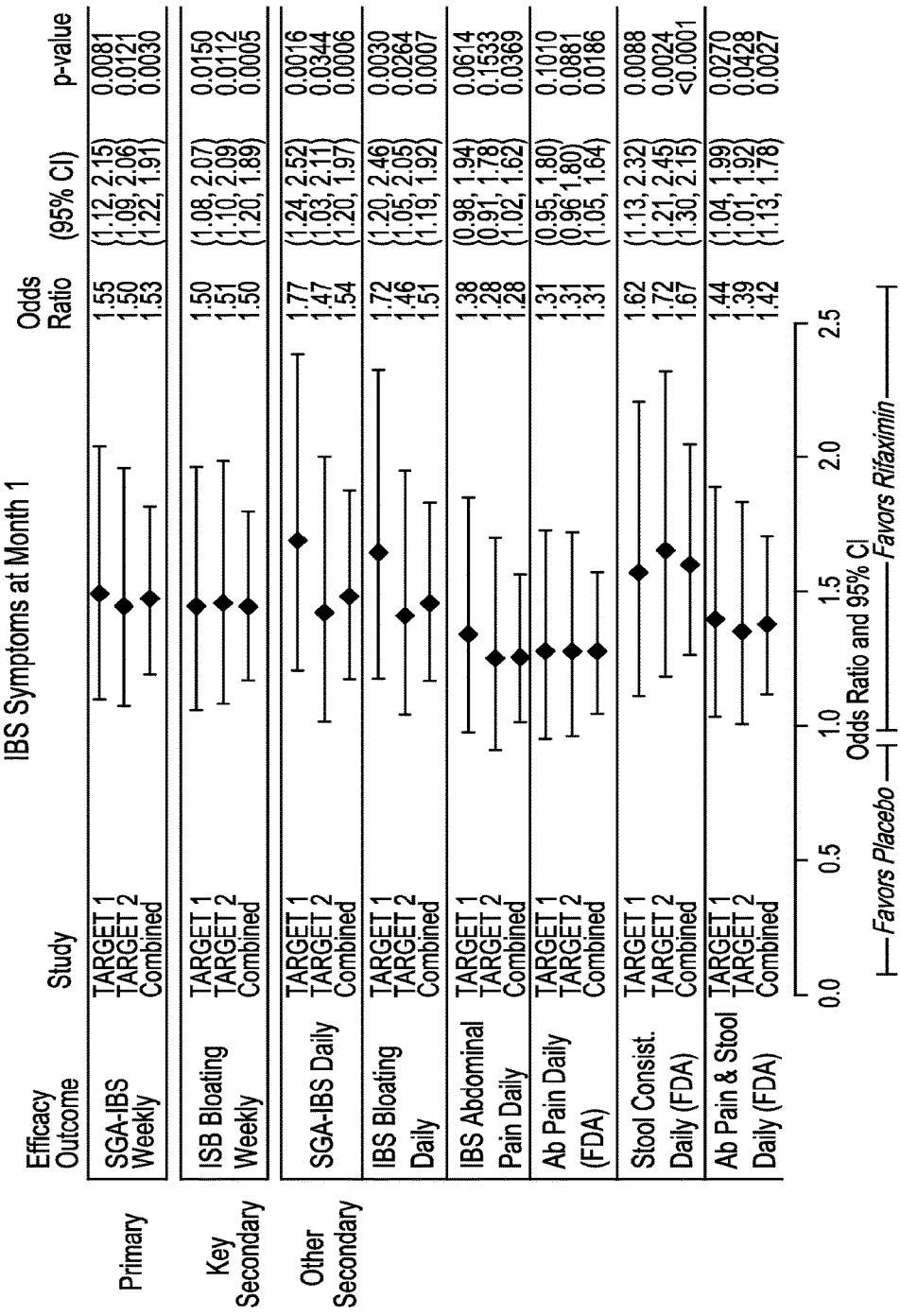
FIG. 11 shows relief of IBS symptoms for the first 4 weeks.
Figure 12:
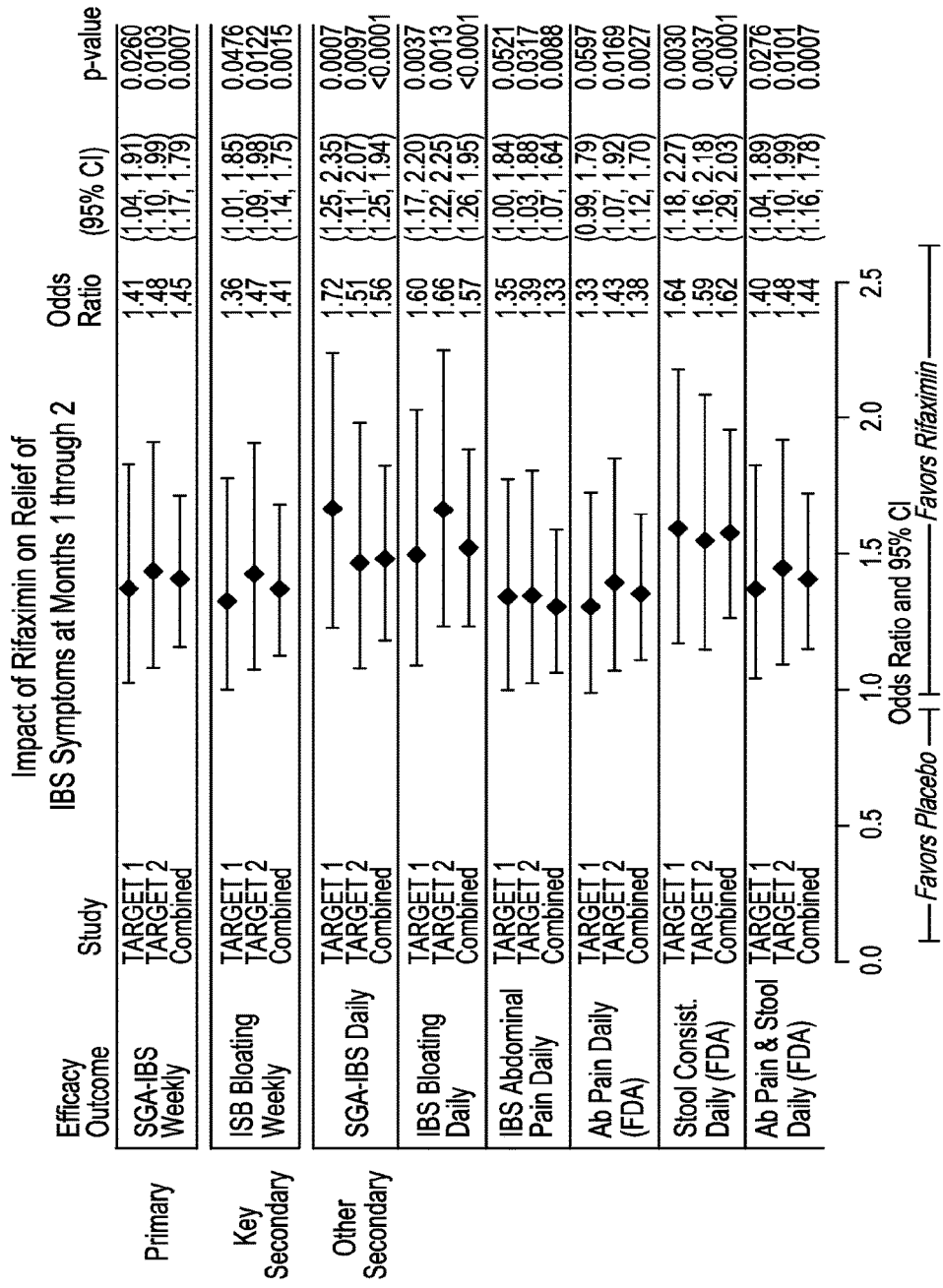
FIG. 12 shows relief of IBS symptoms for the first two months.
Figure 13:
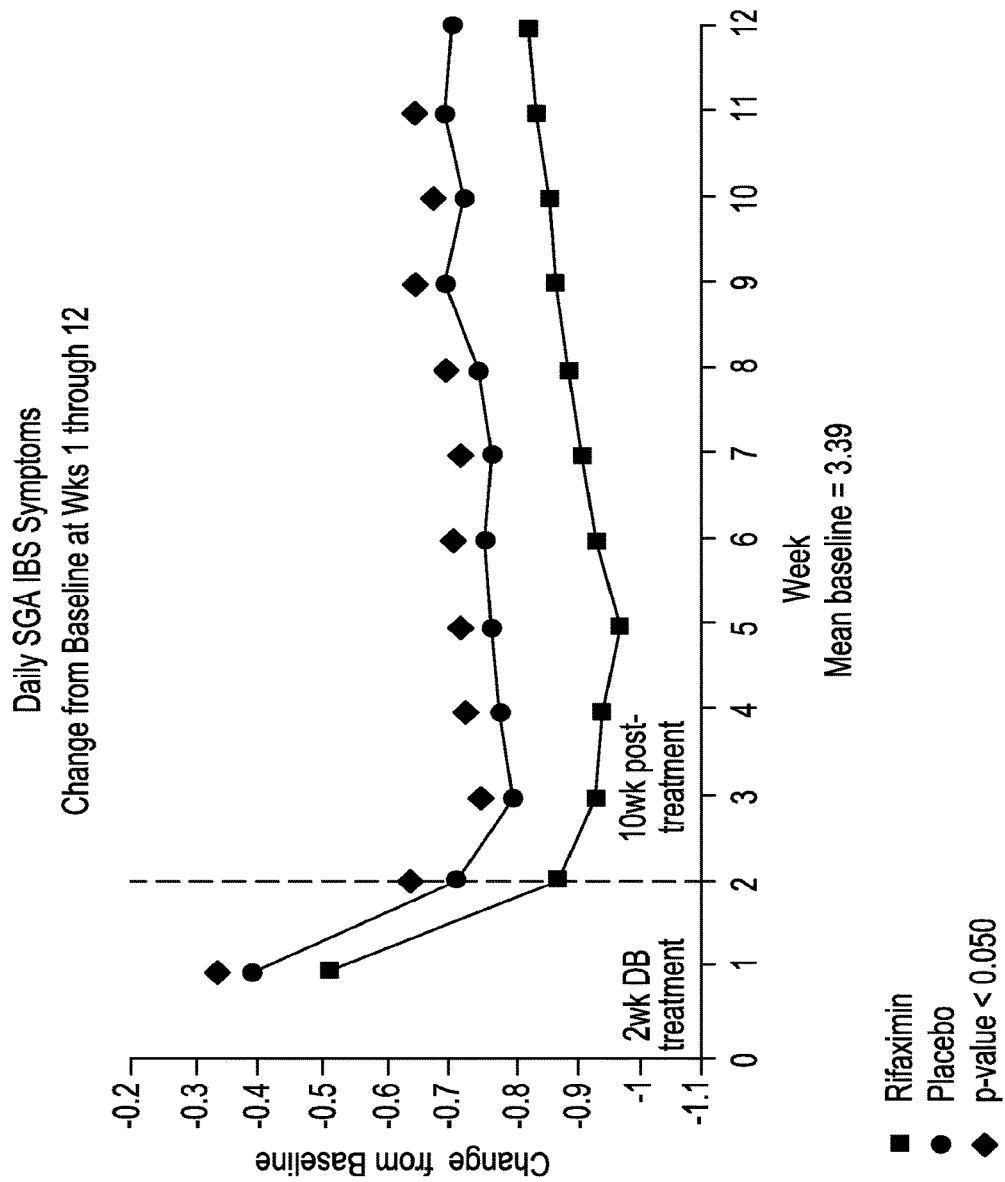
FIG. 13 shows daily IBS symptoms weeks 1 through 12.

The effect of treatment on the percentage of subjects who reported adequate relief of IBS and bloating symptoms for at least two of the final three weeks during the treatment phase (Weeks 1 to 4) is shown in Tables 3-5 and FIGS. 4-6 below.

During the treatment phase, 52.4% of subjects on RFX 550 mg BID met the IBS symptoms responder criterion, compared with 44.2% of the placebo subjects (odds ratio of 1.6 and p value=0.0314). Similarly, 46.1% of subjects in the 550 mg BID group met the bloating symptom responder criterion, compared with 39.6% of the placebo group (odds ratio of 1.6 and p value=0.0402).

TABLE 3

Percentage of Subjects with Adequate Relief of IBS and Bloating Symptoms - ITT Population

| Measure | Placebo [N = 197] | RFX 550 mg BID [N = 191] | Odds Ratio Estimate (95% CI) | P-Value |
|---|---|---|---|---|
| IBS Symptoms | 44.2% | 52.4% | 1.60 (1.04, 2.45) | 0.0314 |
| Bloating Symptom | 39.6% | 46.1% | 1.58 (1.02, 2.45) | 0.0402 |

TABLE 4

Percentage of Subjects with Number of Weeks with Adequate Relief of IBS Symptoms - ITT Population

| | Placebo [N = 197] | RFX 550 mg BID [N = 191] | Odds Ratio Estimate | P-Value |
|---|---|---|---|---|
| Number of Weeks - IBS Symptoms | | | 1.54 (1.07, 2.24) | 0.0216 |
| 0 | 45% | 33% | | |
| 1 | 7% | 11% | | |
| 2 | 15% | 15% | | |
| 3 | 16% | 23% | | |
| | 15% | 16% | | |

TABLE 5

Percentage of Subjects with Number of Weeks with Adequate Relief of Bloating Symptoms - ITT Population

|  | Placebo [N = 197] | RFX 550 mg BID [N = 191] | Odds Ratio Estimate | P-Value |
|---|---|---|---|---|
| Number of Weeks - Bloating Symptom |  |  | 1.57 (1.08, 2.29) | 0.0182 |
| 0 | 47% | 35% |  |  |
| 1 | 10% | 14% |  |  |
| 2 | 12% | 15% |  |  |
| 3 | 15% | 20% |  |  |
| 4 | 13% | 14% |  |  |

Daily Symptom Score

Subjects recorded the following information on dIBS symptoms daily throughout the duration of the study:
  Number of normal stools/day;
  Number of hard and lumpy stools/day;
  Number of loose or watery stools/day;
  Number of loose or watery stools/day with the symptom of urgency;
  How bothersome is abdominal pain and discomfort? [7-point response scale: 0 (not at all) to 6 (a very great deal)];
  How bothersome is bloating? [(7-point response scale: 0 (not at all) to 6 (a very great deal)].

Changes from baseline variables were computed for each weekly summary score.

Long Term Follow-Up of Adequate Relief

Figure 2:
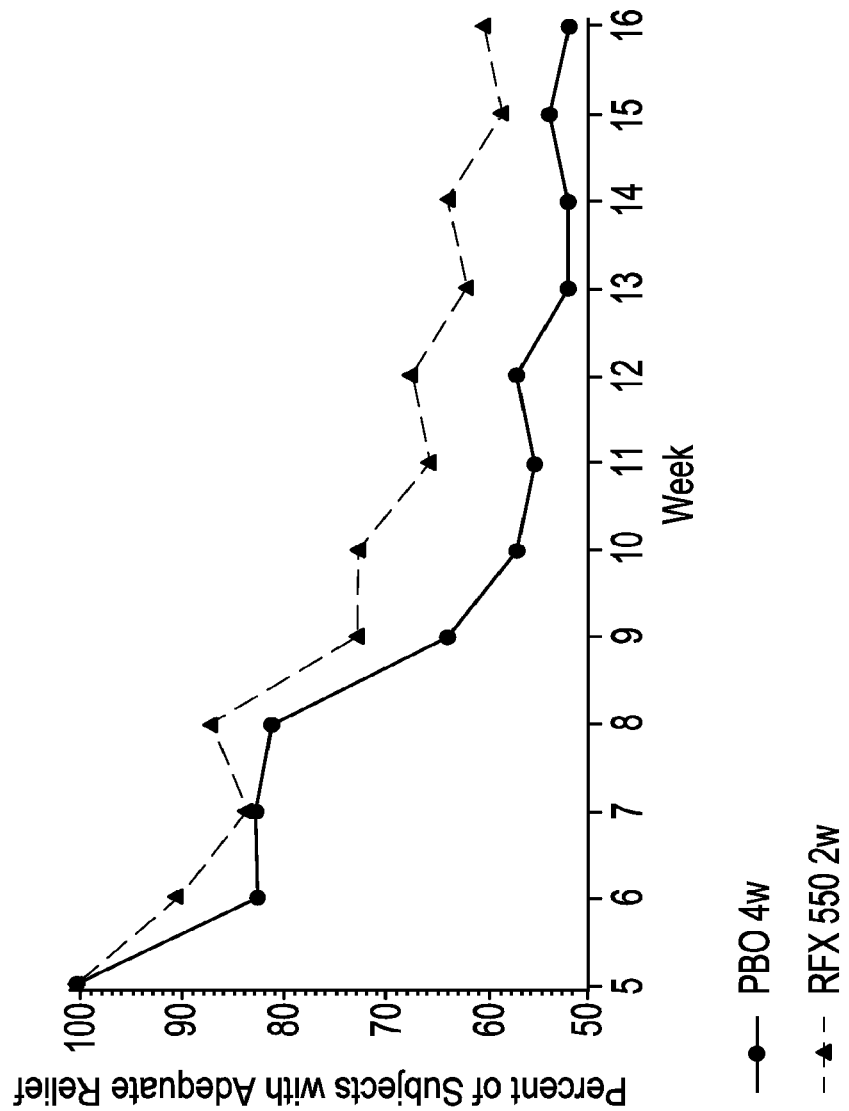
FIG. 2 shows a graph of continuous adequate relief of bloating symptoms during non-treatment follow-up.

The study assessed the effect over 12 weeks of follow-up on long-term adequate relief. Subjects who had adequate relief by Week 4 and remained symptom-free at Week 5 were followed during the post-treatment phase and shown in FIGS. 1 and 2. Superiority to placebo was maintained during the 12 weeks post-treatment follow-up. Results for IBS symptoms were RFX 550 mg BID 62.3% versus placebo 49.2%, and RFX 550 mg BID 59.3% versus 50.9% for placebo for the symptom of bloating through week 16. In assessing the follow-up data, there was statistical significance (p<0.05) of bloating and IBS symptoms for RFX 550 mg BID versus placebo.

TABLE 6

| Adequate Relief of Bloating, Post Treatment | | PBO 4 w (N = 57) n (%) | RFX 550 2 w (N = 54) n (%) |
|---|---|---|---|
| Week 6 | Success | 47 (82.5%) | 49 (90.7%) |
|  | Failures | 10 (17.5%) | 5 (9.3%) |
| Comparison of RFX 550 2 w vs. PBO p-value: 0.1303, odds ratio: 3.840 (0.672, 21.95) | | | |
| Week 7 | Success | 47 (82.5%) | 45 (83.3%) |
|  | Failures | 10 (17.5%) | 9 (16.7%) |
| Comparison of RFX 550 2 w vs. PBO p-value: 0.1311, odds ratio: 2.931 (0.726, 11.84) | | | |
| Week 8 | Success | 46 (80.7%) | 47 (87.0%) |
|  | Failures | 11 (19.3%) | 7 (13.0%) |
| Comparison of RFX 550 2 w vs. PBO p-value: 0.2858, odds ratio: 2.107 (0.536, 8.276) | | | |
| Week 9 | Success | 36 (63.2%) | 39 (72.2%) |
|  | Failures | 21 (36.8%) | 15 (27.8%) |
| Comparison of RFX 550 2 w vs. PBO p-value: 0.0814, odds ratio: 2.737 (0.882, 8.492) | | | |
| Week 10 | Success | 32 (56.1%) | 39 (72.2%) |
|  | Failures | 25 (43.9%) | 15 (27.8%) |
| Comparison of RFX 550 2 w vs. PBO p-value: 0.0217, odds ratio: 3.828 (1.217, 12.04) | | | |
| Week 11 | Success | 31 (54.4%) | 35 (64.8%) |
|  | Failures | 26 (45.6%) | 19 (35.2%) |
| Comparison of RFX 550 2 w vs. PBO p-value: 0.0398, odds ratio: 3.115 (1.054, 9.205) | | | |

TABLE 7

| Adequate Relief of Bloating, Post Treatment | | PBO 4 w (N = 57) n (%) | RFX 550 2 w (N = 54) n (%) |
|---|---|---|---|
| Week 12 | Success | 32 (56.1%) | 36 (66.7%) |
|  | Failure | 25 (43.9%) | 18 (33.3%) |
| Comparison of RFX 550 2 w vs. PBO p-value: 0.0596, odds ratio: 2.891 (0.958, 8.726) | | | |
| Week 13 | Success | 29 (50.9%) | 33 (61.1%) |
|  | Failure | 28 (49.1%) | 21 (38.9%) |
| Comparison of RFX 550 2 w vs. PBO p-value: 0.0142, odds ratio: 4.187 (1.333, 13.15) | | | |
| Week 14 | Success | 29 (50.9%) | 34 (63.0%) |
|  | Failure | 28 (49.1%) | 20 (37.0%) |
| Comparison of RFX 550 2 w vs. PBO p-value: 0.0121, odds ratio: 4.230 (1.372, 13.05) | | | |
| Week 15 | Success | 30 (52.6%) | 31 (57.4%) |
|  | Failure | 27 (47.4%) | 23 (42.6%) |
| Comparison of RFX 550 2 w vs. PBO p-value: 0.0391, odds ratio: 3.323 (1.062, 10.40) | | | |
| Week 16 | Success | 29 (50.9%) | 32 (59.3%) |
|  | Failure | 28 (49.1%) | 22 (40.7%) |
| Comparison of RFX 550 2 w vs. PBO p-value: 0.0212, odds ratio: 3.700 (1.216, 11.25) | | | |

TABLE 8

Baseline Disease Characteristics Across All Treatment Groups

| Daily Symptom | Median | Min, Max |
|---|---|---|
| Total No. bowel movements/day | 3.0 | 1, 15 |
| No. loose/watery bowel movements/day | 2.0 | 0, 10 |
| No. loose/watery with urgency | 1.6 | 0, 10 |
| Abdominal pain/discomfort* | 3.4 | 0, 6 |
| Bloating* | 3.4 | 0, 6 |

*7 pt. scale asking "How bothersome . . . " [0 = not at all to 6 = a very great deal]

Two measures of efficacy were assessed independently. The first was the proportion of subjects who provided a 'yes' response to the weekly SGA question: "In the past 7 days, have you had adequate relief of your IBS symptoms? (yes/no)". The second endpoint was the proportion of subjects who provide a 'yes' response to the weekly individual symptom question: "In the past 7 days, have you had adequate relief of your symptom of bloating? (yes/no)". Durability was based on the proportion of subjects that had adequate relief over the entire treatment phase.

TABLE 9

Summary of Correlation between Subjects Satisfied with
Relief of Bloating Discomfort and Relief of IBS Symptoms

| Time Point | Number of Subjects | Relief [1] | Responder [2] | Non-Responder [2] | Spearman Correlation Coefficient |
|---|---|---|---|---|---|
| Week 1 | 680 | Yes | 49/169 (29.0%) | 45/511 (8.8%) | 0.2508 |
|  |  | No | 120/169 (71.0%) | 458/511 (89.6%) |  |
|  |  | Missing |  | 8/511 (1.6%) |  |
| Week 2 | 680 | Yes | 131/274 (41.2%) | 50/406 (12.3%) | 0.3218 |
|  |  | No | 159/274 (58.0%) | 327/406 (80.5%) |  |
|  |  | Missing | 2/274 (0.7%) | 29/406 (7.1%) |  |
| Week 3 | 680 | Yes | 130/303 (42.9%) | 48/377 (12.7%) | 0.3201 |
|  |  | No | 169/303 (55.8%) | 281/377 (74.5%) |  |
|  |  | Missing | 4/303 (1.3%) | 48/377 (12.7%) |  |
| Week 4 | 680 | Yes | 145/309 (46.9%) | 52/371 (14.0%) | 0.3362 |
|  |  | No | 153/309 (49.5%) | 252/371 (67.9%) |  |
|  |  | Missing | 11/309 (3.6%) | 67/371 (18.1%) |  |

[1] Responses to the questions 'How bothersome was your bloating today?' include: 0 = not at all, 1 = hardly, 2 = somewhat, 3 = moderately, 4 = a good deal, 5 = a great deal, 6 = a very great deal; Relief is score of 0 or 1.
[2] Responder is defined as relief of IBS symptoms.

TABLE 10

Efficacy Analysis:
Adequate Relief of IBS Symptoms and Bloating at the End of the Treatment Phase

| Gender |  | PBO 4 w (N = 197) n (%) | RFX 275 2 w (N = 95) n (%) | RFX 550 2 w (N = 191) n (%) | RFX 550 2 w (N = 99) n (%) | RFX 550 4 w (N = 98) n (%) |
|---|---|---|---|---|---|---|
|  | Adequate Relief of IBS Symptoms [1] |  |  |  |  |  |
| Male | Success |  | 17 (32.7%) | 5 (35.7%) | 29 (53.7%) | 12 (46.2%) | 7 (31.8%) |
|  | Failure |  | 35 (67.3%) | 9 (64.3%) | 25 (46.3%) | 14 (53.8%) | 15 (68.2%) |
|  | Comparison of RFX 550 2 w vs. PBO p-value: 0.0326, odds ratio: 2.511 (1.079, 5.842) |  |  |  |  |  |
|  | Adequate Relief of Bloating [2] |  |  |  |  |  |
|  | Success |  | 17 (32.7%) | 6 (42.9%) | 25 (46.3%) | 10 (38.5%) | 6 (27.3%) |
|  | Failure |  | 35 (67.3%) | 8 (57.1%) | 29 (53.7%) | 16 (61.5%) | 16 (72.7%) |
|  | Comparison of RFX 550 2 w vs. PBO p-value: 0.0802, odds ratio: 2.148 (0.912, 5.057) |  |  |  |  |  |
|  | Adequate Relief of IBS Symptoms [1] |  |  |  |  |  |
| Female | Success |  | 70 (48.3%) | 35 (43.2%) | 71 (51.8%) | 29 (39.7%) | 34 (44.7%) |
|  | Failure |  | 75 (51.7%) | 46 (56.8%) | 66 (48.2%) | 44 (60.3%) | 42 (55.3%) |
|  | Comparison of RFX 550 2 w vs. PBO p-value: 0.7608, odds ratio: 1.078 (0.665, 1.747) |  |  |  |  |  |
|  | Adequate Relief of Bloating [2] |  |  |  |  |  |
|  | Success |  | 61 (42.1%) | 29 (35.8%) | 63 (46.0%) | 28 (38.4%) | 32 (42.1%) |
|  | Failure |  | 84 (57.9%) | 52 (64.2%) | 74 (54.0%) | 45 (61.6%) | 44 (57.9%) |
|  | Comparison of RFX 550 2 w vs. PBO p-value: 0.5366, odds ratio: 1.166 (0.716, 1.898) |  |  |  |  |  |

[1] Subjects achieved success if they reported a 'yes' response to whichever question about IBS symptoms was posed by the IVR system(i.e. adequate relief or control) for = 2 out of the 3 final treatment weeks.
[2] Subjects achieved success if they reported a 'yes' response to whichever question about symptoms of bloating was posed by the IVR system (i.e. adquate relief or control) for = 2 out of the 3 final treatment weeks.

The treatment effect is more pronounced when accounting for milder disease severity, i.e., bloating, abdominal pain/discomfort and bowel movements.

Example 2

Figure 3:
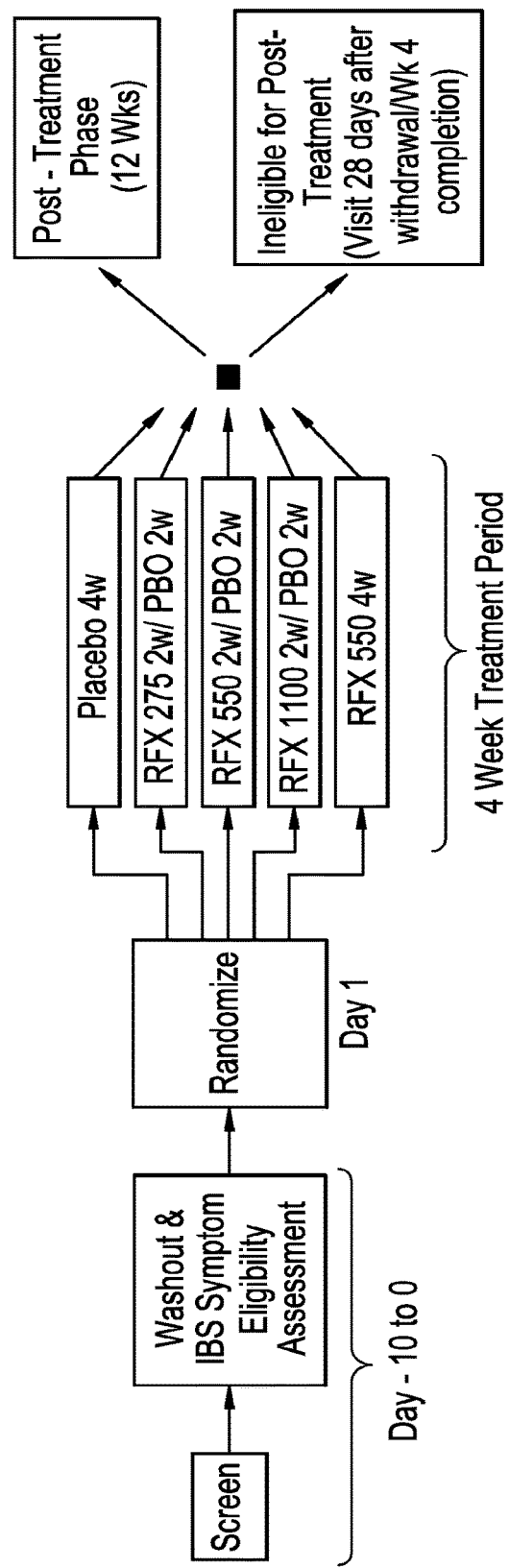
FIG. 3 shows proposed study design for treatment with rifaximin to show durability of response.

A study (FIG. 3) is designed to evaluate the efficacy of a 14-day course of oral rifaximin at 550 mg TID in providing adequate relief from diarrhea-associated IBS (dIBS) symptoms over four weeks. A measure of efficacy is based on subjects' answers to the Weekly Subject Global Assessment (SGA) questions over the 4 week study duration in relation to their IBS symptoms. The SGA question is asked weekly as follows: "In the past 7 days, have you had adequate relief of your IBS symptoms?" (Yes/No.) Subjects in the treatment group taking oral rifaximin respond "Yes" more often than Subjects who are not taking oral rifaximin. Another measure of efficacy is based on subjects' answers to the Weekly Subject Global Assessment (SGA) question over the 4 week study duration in relation to their IBS symptom of bloating. The SGA question is asked weekly as follows: "In the past 7 days, have you had adequate relief of your IBS symptom of bloating?" (Yes/No. Subjects in the treatment group taking oral rifaximin respond "Yes" more often than subjects who are not taking oral rifaximin. Other measures of efficacy include the changes in dIBS symptoms from baseline to each week of the 4 weeks in the study (e.g., abdominal pain and discomfort, bloating, number of stools per day, stool consistency, urgency with loose or watery stools).

Example 3

Improvements in Quality of Life

A study showed the rifaximin 550 mg twice daily (BID) significantly improved IBS symptoms versus placebo in patients with diarrhea-predominant IBS (dIBS). Analyses from that study evaluated the efficacy of rifaximin for improving quality of life (QOL) measures in patients with dIBS.

Adults diagnosed with dIBS (Rome II criteria) received rifaximin 550 mg BID or placebo for 14 days. Both groups received placebo for an additional 14 days after the initial 2-week treatment. Quality of life was assessed with the 34-item IBS-QOL questionnaire at baseline and 4 weeks after initiating treatment. Each item was scored on a 5-point scale (1=not at all; 2=slightly; 3=moderately; 4=quite a bit; and 5=extremely or a great deal). Results for composite and subscale scores were converted to a scale ranging from 0 to 100, with higher scores indicating better QOL.

A total of 388 patients were treated; 191 patients received rifaximin and 197 patients received placebo during the 2-week initial treatment period. The mean improvement from baseline in overall QOL scores at week 4 was significantly greater with rifaximin compared with placebo (Table 11). Patients in the rifaximin group reported significantly greater mean improvement from baseline in QOL scores for dysphoria, body image, health worry, social reaction, and relationship subscales compared with placebo (Table 11). Rifaximin was well tolerated, with similar incidence of adverse events compared with placebo.

In patients with IBS-D, rifaximin 1100 mg/d for 14 days significantly improved QOL measures compared with placebo. These findings suggest a potential therapeutic role for rifaximin 550 mg BID for improving symptoms and QOL in patients with IBS-D and are summarized in Table 11.

TABLE 11

Mean Change From Baseline in IBS-QOL Scores at Week 4

| Domain | Rifaximin 1100 mg/d (n = 191) | Placebo (n = 197) | Improvement with rifaximin over placebo, % | P value |
| --- | --- | --- | --- | --- |
| Overall score | 20.4 | 15.8 | 28.7 | 0.020 |
| Dysphoria | 24.8 | 19.8 | 25.3 | 0.027 |
| Interference with activity | 22.2 | 18.1 | 22.2 | 0.083 |
| Body image | 20.1 | 14.6 | 37.4 | 0.012 |
| Health worry | 16.0 | 12.2 | 30.6 | 0.047 |
| Food avoidance | 25.0 | 20.5 | 22.1 | 0.088 |
| Social reaction | 17.3 | 13.2 | 31.6 | 0.047 |
| Sexual | 13.6 | 10.9 | 24.9 | 0.199 |
| Relationship | 14.9 | 10.7 | 39.5 | 0.030 |

A 2-week course of rifaximin (1100 mg/day) significantly improved quality of life (QOL) measures, compared with placebo.

In a study, 191 adult patients diagnosed with diarrhea-predominant IBS (dIBS) by Rome II criteria were randomized to receive rifaximin 550 mg twice daily (BID) and 197 patients were randomized to placebo. Following a 2-week initial treatment period, both groups of patients received placebo for an additional 14 days. Quality of life was assessed via the 34-item IBS-QOL questionnaire at baseline and 4 weeks after initiating treatment. Each item was scored on a 5-point scale (1=not at all; 2=slightly; 3=moderately; 4=quite a bit; 5=extremely or a great deal); results for composite and subscale scores were converted to a scale ranging from 0 to 100, with higher scores indicating better QOL.

At Week 4, the mean improvement from baseline in the overall QOL score was significantly greater with rifaximin compared with placebo (20.4 vs. 15.8, respectively; p=0.020). Patients in the rifaximin group also reported significantly greater mean improvement from baseline in QOL subscale scores for dysphoria (restlessness or agitation, 24.8 vs. 19.8; p=0.027), body image (20.1 vs. 14.6; p=0.012), health worry (16.0 vs. 12.2; p=0.047), social reaction (17.3 vs. 13.2; p=0.047), and relationships (14.9 vs. 10.7; p=0.030), compared with placebo. Rifaximin was well tolerated in the study, with a similar incidence of adverse events compared with placebo.

Example 4

Severity of Baseline Symptoms as Predictor of Clinical Response

It is reported herein that the severity of baseline symptoms of abdominal pain and bloating influenced the response to rifaximin treatment. The co-primary endpoints in this analysis assessed weekly yes/no responses to questions regarding adequate relief of global IBS symptoms and IBS-associated bloating. Severity of baseline IBS symptoms was evaluated as a potential confounder of clinical response and was categorized as mild/moderate or severe based on a mean score of ≤4 vs. >4 (on a 7-point scale) for bloating and abdominal pain.

A significantly larger percentage of patients treated with rifaximin reported adequate relief of global IBS symptoms (52% vs. 44% for placebo; p=0.03) and bloating (46% vs. 40%; p=0.04), compared with placebo-treated patients. In patients with mild/moderate abdominal pain, rifaximin produced a greater degree of improvement, compared with placebo, in global symptoms of IBS (50% vs. 39%, respectively; p=0.04) and bloating (44% vs. 35%; p=0.09). Similarly, in patients with mild/moderate bloating, rifaximin treatment was associated with greater improvement, compared with placebo, in global IBS symptoms (56% vs. 41%, respectively; p=0.006) and bloating (47% vs. 36%; p=0.03). This demonstrates that patients with mild/moderate IBS symptoms are more likely than those with severe disease to achieve symptomatic relief with rifaximin.

These results show that rifaximin improves gastrointestinal (GI) symptoms associated with IBS. In this study of rifaximin versus placebo, patients with diarrhea-predominant IBS (IBS-D) were studied, a supplemental analysis examined the association between severity of baseline IBS symptoms and clinical response to rifaximin.

A comparison involved 2 groups of adult patients with IBS-D (Rome II) who received rifaximin 550 mg twice daily or placebo for 14 days, followed by an additional 14 days of placebo in both groups. The Weekly yes/no responses to questions regarding adequate relief of global IBS symptoms and IBS-associated bloating were assessed. Clinical response was defined as adequate relief for 2 of the final 3 treatment weeks (wk 2, 3, or 4). Severity of baseline IBS symptoms was evaluated as a potential confounder of clinical response and was categorized as mild/moderate or severe based on a mean score of ≤4 versus >4 (on a 7-point scale (0=not bothersome; 6=very bothersome)) for bloating and abdominal pain.

A significantly larger percentage of patients who received rifaximin versus placebo reported adequate relief of global IBS symptoms (52% versus 44%, respectively; P=0.03) and bloating (46% versus 40%, respectively; P=0.04). In patients with mild/moderate abdominal pain, rifaximin produced a greater degree of improvement versus placebo in symptoms of IBS (50% versus 39%, respectively; P=0.04) and bloating (44% versus 35%, respectively; P=0.09). In patients with mild/moderate bloating, rifaximin also achieved greater improvement versus placebo in global symptoms of IBS (56% versus 41%, respectively; P=0.006) and bloating (47% versus 36%, respectively; P=0.03). Severity of baseline symptoms of abdominal pain and bloating influenced the response to rifaximin 1100 mg/d for 14 days. Patients with mild/moderate IBS symptoms had a greater likelihood of relief of global IBS-related symptoms with rifaximin treatment versus individuals with severe IBS symptoms.

Example 5

A study was designed to evaluate the efficacy of a 14-day course of oral rifaximin at 550 mg TID in providing adequate relief from diarrhea-predominant IBS (dIBS) symptoms over four weeks. A measure of efficacy is based on subjects' answers to the Weekly Subject Global Assessment (SGA) questions over the 4 week study duration in relation to their IBS symptoms. The SGA question is asked weekly as follows: "In the past 7 days, have you had adequate relief of your IBS symptoms?" (Yes/No.) Subjects in the treatment group taking oral rifaximin respond "Yes" more often than Subjects who are not taking oral rifaximin. Another measure of efficacy is based on subjects' answers to the Weekly Subject Global Assessment (SGA) question over the 4 week study duration in relation to their IBS symptom of bloating. The SGA question is asked weekly as follows: "In the past 7 days, have you had adequate relief of your IBS symptom of bloating?" (Yes/No). Subjects in the treatment group taking oral rifaximin respond "Yes" more often than subjects who are not taking oral rifaximin. Other measures of efficacy include the changes in dIBS symptoms from baseline to each week of the 4 weeks in the study (e.g., abdominal pain and discomfort, bloating, number of stools per day, stool consistency, urgency with loose or watery stools).

The randomized, double-blind, placebo-controlled, multicenter trial was designed to evaluate the efficacy and safety of rifaximin 550 mg TID in the treatment of patients with nonconstipation irritable bowel syndrome (non-C IBS). In the trial rifaximin versus placebo treated patients demonstrated a statistically significant improvement for the primary endpoint of the adequate relief of IBS symptoms as assessed over one month (weeks 3, 4, 5 and 6) following completion of a 14-day course of therapy (weeks 1 and 2). Consistent with the primary endpoint in each trial, the key secondary endpoint of relief of IBS-related bloating also demonstrated statistical significance of rifaximin versus placebo in each trial.

The study was designed to assess the clinical efficacy and safety of a 550 mg TID dosing regimen of rifaximin (1650 mg/day) compared with placebo in a broad population comprised of males and females 18 years of age and older who have been diagnosed with non-constipation IBS, e.g., diarrhea-predominant IBS or alternating IBS. The primary efficacy endpoint of the study was the proportion of subjects who achieve adequate relief of IBS symptoms for at least 2 weeks during 10 the first 4 weeks of the 10-week follow-up phase.

Subjects received 550 mg of rifaximin three times daily (TID) for 14 days and then were followed for 10 weeks for study duration of 12 weeks. Two measures of efficacy were assessed. Subjects were questioned on the relief of overall IBS symptoms and bloating. Adequate relief of IBS related symptoms (SGA) and IBS-related bloating (IBS-B) were assessed, and a dose of 550 mg TID 15 for 2 weeks demonstrated statistically significant relief. The analyses defined success as a "yes" response to questions regarding adequate relief.

A measure of efficacy is based on subjects' answers to the Weekly Subject Global Assessment (SGA) questions over the 4 week study duration in relation to their IBS symptoms. The SGA question is asked weekly as follows: "In the past 7 days, have you had adequate relief of your 20 IBS symptoms?" (Yes/No.) Subjects in the treatment group taking oral rifaximin respond "Yes" more often than Subjects who are not taking oral rifaximin. Another measure of efficacy is based on subjects' answers to the Weekly Subject Global Assessment (SGA) question over the 4 week study duration in relation to their IBS symptom of bloating. The SGA question is asked weekly as follows: "In the past 7 days, have you had adequate relief of your IBS symptom of bloating?" (Yes/No). Subjects in the treatment group taking oral rifaximin respond "Yes" more often than subjects who are not taking oral rifaximin.

All subpopulations in the study responded to therapy. Baseline severity was determined during screening for Abdominal Pain/Discomfort and Bloating, and the number, type (normal, hard, loose) and urgency of bowel movements. Duration of effect was assessed in a ten week follow-up period.

Study Demographics

Subjects enrolled in the study are detailed in Table 13. Demographics of the population are set forth in Tables 14, 15, and 16.

Rifaximin Exposure

Rifaximin exposure in subjects having IBS is similar to the levels of exposure in healthy subjects and more than 520-fold lower than rifampin exposure, and more than 66-fold lower than neomycin exposure. As previously disclosed by Applicants, the rifaximin exposure in healthy subjects is significantly lower than the level of exposure in subjects having hepatic encephalopathy.

Percentage of Subjects with Adequate Relief of IBS and Bloating Symptoms

The primary and secondary endpoints evaluated in this study were the effect of treatment on the percentage of subjects who reported adequate relief of IBS and the adequate relief of IBS symptom of bloating. These results are shown in Tables 17, 18, 19 and 20. The data demonstrates that more subjects taking rifaximin had adequate relief of IBS symptoms and of bloating.

To further evaluate the study results, efficacy of rifaximin treatment on subpopulations of study participants was evaluated.

Primary and secondary endpoints were evaluated for male and female populations independently. This analysis indicated that higher percentage of female subjects taking rifaximin had adequate relief of IBS symptoms and the IBS symptom of bloating. See Table 21.

Primary and secondary endpoints were evaluated for subpopulations of study participants based on age. Analysis of subjects less than 65 and those 65 years old and older demonstrated that a higher percentage of subjects 65 years old or older that were administered rifaximin had adequate relief of IBS symptom of bloating. See Table 22.

The efficacy of rifaximin treatment of white and non-white study participants demonstrated that a higher percentage of non-white participants administered rifaximin had adequate relief of IBS symptoms. See Table 23.

The efficacy of rifaximin treatment was also evaluated for subjects having diarrhea-predominant IBS and alternating-predominant IBS. The data indicate that a higher percentage of subjects having alternating-predominant IBS had adequate relief of IBS symptoms and adequate relief of IBS symptom of bloating than subjects with diarrhea-predominant. See Table 24.

The study also evaluated the effect of rifaximin administration on the average number of stools per day from the baseline value for each subject. The data indicate that rifaximin effectively decreased the weekly average of stool frequency by at least one for subjects in the study. In particular, the last four weeks of the study show significant decrease in the stool frequency for subject administered rifaximin when compared to those administered a placebo. See Table 25.

TABLE 25

Stool frequency (SF).

| Week | Placebo % with decrease in SF | Rifaximin (550 mg TID)% with decrease in SF | P-value |
|---|---|---|---|
| 1 | 16.9 | 14.4 | .3853 |
| 2 | 21.6 | 20.6 | .7562 |
| 3 | 23.1 | 22.2 | .7677 |
| 4 | 24.1 | 21.6 | .4464 |
| 5 | 21.3 | 25.7 | .1901 |
| 6 | 23.4 | 22.9 | .8402 |
| 7 | 23.8 | 23.8 | .9945 |
| 8 | 20.9 | 24.4 | .3029 |
| 9 | 24.7 | 25.4 | .8581 |
| 10 | 21.6 | 26.7 | .1360 |
| 11 | 24.1 | 25.4 | .6994 |
| 12 | 25.3 | 27.0 | .6390 |

Interestingly, subjects administered 550 mg rifaximin TID showed a decrease in skin and subcutaneous tissue disorders as compared to the placebo group. 3.8% of the placebo group had skin or subcutaneous tissue disorders as compared to 1.3% of the rifaximin treated group.

TABLE 13

Subject Disposition by Treatment Group Population: Randomized Subjects

|  | Placebo n (%) | Rifaximin 550 mgTID n (%) | Total n (%) |
|---|---|---|---|
| Subjects Randomized | 321 | 316 | 637 |
| Intent-to-Treat Subjects [1] | 320 (99.7%) | 315 (99.7%) | 635 (99.70%) |
| Subjects Completed the Treatment Phase | 313 (97.5%) | 310 (98.1%) | 623 (97.80%) |
| Subjects Completed through Week 6 | 307 (95.6%) | 308 (97.5%) | 615 (96.50%) |
| Subjects Completed the Study | 302 (94.1%) | 301 (95.3%) | 603 (94.70%) |
| Subjects Discontinued Study Early | 19 (5.9%) | 15 (4.7%) | 34 (5.30%) |
| Primary Reason For Early Discontinuation of Study | | | |
| Adverse Event/Serious Adverse Event | 2 (0.6%) | 0 | 2 (0.30%) |
| Subject Request | 8 (2.5%) | 6 (1.9%) | 14 (2.20%) |
| Lost to Follow-Up | 6 (1.9%) | 6 (1.9%) | 12 (1.90%) |
| Noncompliance | 2 (0.6%) | 1 (0.3%) | 3 (0.50%) |
| Pregnancy | 0 | 0 | 0 |
| Other | 1 (0.3%) | 2 (0.6%) | 3 (0.50%) |

Note:
Percentage calculation is based on the number of subjects randomized.
[1] Intent-to-Treat population includes all randomized subjects who ingested at least one dose of the study drug.

TABLE 14

Summary of Demographic by Treatment Group: Population: ITT

|  | mg TID (N = 320) | Total (N = 315) | (N = 635) |
|---|---|---|---|
| Age (years) | | | |
| n | 320 | 315 | 635 |
| Mean | 46.3 | 45.9 | 46.1 |
| SD | 14.57 | 13.87 | 14.22 |
| Median | 46 | 45 | 46 |
| Min | 18 | 19 | 18 |
| Max | 82 | 88 | 88 |
| Age group - n (%) | | | |
| <65 | 283 (88.4%) | 285 (90.5%) | 568 (89.4%) |
| >=65 | 37 (11.6%) | 30 (9.5%) | 67 (10.6%) |
| Gender - n (%) | | | |
| Male | 95 (29.7%) | 88 (27.9%) | 183 (28.8%) |
| Female | 225 (70.3%) | 227 (72.1%) | 452 (71.2%) |
| Race [1] - n (%) | | | |
| American Indian or Alaskan Native | 2 (0.6%) | 1 (0.3%) | 3 (0.5%) |
| Asian | 2 (0.6%) | 6 (1.9%) | 8 (1.3%) |
| Black or African American | 14 (4.4%) | 21 (6.7%) | 35 (5.5%) |
| Native Hawaiian or Other Pacific Islander | 0 | 3 (1.0%) | 3 (0.5%) |
| White | 302 (94.4%) | 282 (89.5%) | 584 (92.0%) |
| Other | 0 | 2 (0.6%) | 2 (0.3%) |

TABLE 15

Summary of Demographic by Treatment Group Population ITT

|  | Placebo (N = 320) | Rifaximin 550 mg TID (N = 315) | Total (N = 635) |
|---|---|---|---|
| Ethnicity - n (%) | | | |
| Hispanic or Latino | 29 (9.1%) | 29 (9.2%) | 58 (9.1%) |
| Not Hispanic or Latino | 291 (90.9%) | 286 (90.8%) | 577 (90.9%) |
| Height (cm) | | | |
| n | 320 | 315 | 635 |
| Mean | 167.85 | 167.32 | 167.59 |
| SD | 9.684 | 10.342 | 10.011 |
| Median | 167.60 | 165.50 | 167.60 |
| Min | 147.3 | 104.8 | 104.8 |
| Max | 193.0 | 198.1 | 198.1 |
| Weight - n | 320 | 315 | 635 |
| Mean | 81.30 | 80.91 | 81.11 |
| SD | 19.715 | 20.233 | 19.959 |
| Median | 78.95 | 78.90 | 78.90 |

TABLE 15-continued

Summary of Demographic by Treatment Group Population ITT

|  | Placebo (N = 320) | Rifaximin 550 mg TID (N = 315) | Total (N = 635) |
|---|---|---|---|
| Min | 40.8 | 46.7 | 40.8 |
| Max | 161.5 | 166.9 | 166.9 |

Note:
Percentages are based on the number of subjects in the ITT population in each treatment group.
[1] If more than one race are checked, the subject is only included in the 'Other' category.

TABLE 16

Summary of Demographic by Treatment Group Population ITT

|  | Placebo N = 320 | Rifaximin 550 mg TID N = 315 | Total N = 635 |
|---|---|---|---|
| BMI(kg/m^2) |  |  |  |
| n | 320 | 315 | 635 |
| Mean | 28.8 | 28.92 | 28.86 |
| SD | 6.546 | 6.872 | 6.705 |
| Median | 27.6 | 27.8 | 27.7 |
| Min | 15.7 | 17.3 | 15.7 |
| Max | 55.7 | 55.8 | 55.8 |
| BMI (kg/m^2) - Male |  |  |  |
| n | 95 | 88 | 183 |
| Mean | 28.09 | 28.45 | 28.27 |
| SD | 4.903 | 5.526 | 5.2 |
| Median | 27.7 | 27.55 | 27.7 |
| Min | 18.9 | 19.4 | 18.9 |
| Max | 46.6 | 54.3 | 54.3 |
| BMI (kg/m^2) - Female |  |  |  |
| n | 225 | 227 | 452 |
| Mean | 29.1 | 29.11 | 29.1 |
| SD | 7.116 | 7.33 | 7.216 |
| Median | 27.5 | 27.9 | 27.75 |
| Min | 15.7 | 17.3 | 15.7 |
| Max | 55.7 | 55.8 | 55.8 |

TABLE 17

Adequate Relief of IBS Symptoms and IBS Symptom of Bloating by Treatment Group

|  | Placebo (N = 320) n (%) | Rifaximin 550 mg TID (N = 315) n (%) | p-value |
|---|---|---|---|
| Adequate Relief of IBS symptoms [2] |  |  | 0.0256 |
| Success | 100 (31.3%) | 125 (39.7%) |  |
| Failure | 220 (68.8%) | 190 (60.3%) |  |
| Adequate Relief of IBS symptom of Bloating [3] |  |  | 0.0198 |
| Success | 99 (30.9%) | 125 (39.7%) |  |
| Failure | 221 (69.1%) | 190 (60.3%) |  |

Note:
Last observation carried forward method (LOCF) was used to handle missing responses. Baseline responses were not carried forward.
[1] p-value is obtained from a Logistic regression model with fixed effects treatment arm and analysis center.
[2] Subjects achieved success if they answered 'Yes' to the weekly SGA question, 'In the past 7 days, have you had adequate relief of your IBS symptoms', for at least 2 of the first 4 weeks during the follow-up phase (ie, Weeks 3 through 6).
[3] Subjects achieved success if they answered 'Yes' to the weekly SGA question, 'In the past 7 days, have you had adequate relief of your IBS symptom of bloating', for at least 2 of the first 4 weeks during the follow-up phase (ie, Weeks 3 through 6).

TABLE 18

Adequate Relief of IBS Symptoms and IBS Symptom of Bloating by Treatment Group Population: PP

|  | Placebo (N = 310) N (%) | Rifaximin 550 mg TID (N = 311) N (%) | p-value |
|---|---|---|---|
| Adequate Relief of IBS symptoms [2] |  |  | 0.0159 |
| Success | 95 (30.6%) | 124 (39.9%) |  |
| Failure | 215 (69.4%) | 187 (60.1%) |  |
| Adequate Relief of IBS symptom of Bloating [3] |  |  | 0.012 |
| Success | 94 (30.3%) | 124 (39.9%) |  |
| Failure | 216 (69.7%) | 187 (60.1%) |  |

Note:
Subjects failed to meet inclusion criteria 3, 4, 5, or exclusion criteria 1 or 8 are excluded from this table.

Note:
Last observation carried forward method (LOCF) was used to handle missing responses. Baseline responses were not carried forward.
[1] p-value is obtained from a Logistic regression model with fixed effects treatment arm and analysis center.
[2] Subjects achieved success if they answered 'Yes' to the weekly SGA question, 'In the past 7 days, have you had adequate relief of your IBS symptoms', for at least 2 of the first 4 weeks during the follow-up phase (ie, Weeks 3 through 6).
[3] Subjects achieved success if they answered 'Yes' to the weekly SGA question, 'In the past 7 days, have you had adequate relief of your IBS symptom of bloating', for at least 2 of the first 4 weeks during the follow-up phase (ie, Weeks 3 through 6).

TABLE 19

Adequate Relief of IBS Symptoms and IBS Symptom of Bloating Based on Daily Measures by Treatment Group Population: ITT

|  | Placebo (N = 320) N (%) | Rifaximin 550 mg TID (N = 315) N (%) | p-value |
|---|---|---|---|
| Adequate Relief of IBS symptoms [2] |  |  | 0.0139 |
| Success | 88 (27.5%) | 115 (36.5%) |  |
| Failure | 232 (72.5%) | 200 (63.5%) |  |
| Adequate Relief of IBS symptom of Bloating [3] |  |  | 0.0139 |
| Success | 95 (29.7%) | 133 (42.2%) |  |
| Failure | 225 (70.3%) | 182 (57.8%) |  |

Note:
[1] p-value is obtained from a Logistic regression model with fixed effects treatment arm and analysis center.
[2] Subjects achieved success if they answered 'Yes' to the weekly SGA question, 'In the past 7 days, have you had adequate relief of your IBS symptoms', for at least 2 of the first 4 weeks during the follow-up phase (ie, Weeks 3 through 6).
[3] Subjects achieved success if they answered 'Yes' to the weekly SGA question, 'In the past 7 days, have you had adequate relief of your IBS symptom of bloating', for at least 2 of the first 4 weeks during the follow-up phase (ie, Weeks 3 through 6).

TABLE 20

Adequate Relief of IBS Symptoms and IBS Symptom of Bloating Based on Daily Measures by Treatment Group Population: PP

|  | Placebo (N = 310) N (%) | Rifaximin 550 mg TID (N = 311) N (%) | p-value |
|---|---|---|---|
| Adequate Relief of IBS symptoms [2] |  |  | 0.0075 |
| Success | 84 (27.1%) | 115 (37.0%) |  |
| Failure | 226 (72.9%) | 196 (63.0%) |  |
| Adequate Relief of IBS symptom of Bloating [3] |  |  | 0.0012 |

TABLE 20-continued

Adequate Relief of IBS Symptoms and IBS Symptom of Bloating
Based on Daily Measures by Treatment Group Population: PP

|  | Placebo (N = 310) N (%) | Rifaximin 550 mg TID (N = 311) N (%) | p-value |
|---|---|---|---|
| Success | 92 (29.7%) | 131 (42.1%) | |
| Failure | 218 (70.3%) | 180 (57.9%) | |

Note:
[1] p-value is obtained from a Logistic regression model with fixed effects treatment arm and analysis center.
[2] Subjects achieved success if they answered 'Yes' to the weekly SGA question, 'In the past 7 days, have you had adequate relief of your IBS symptoms', for at least 2 of the first 4 weeks during the follow-up phase (ie, Weeks 3 through 6).
[3] Subjects achieved success if they answered 'Yes' to the weekly SGA question, 'In the past 7 days, have you had adequate relief of your IBS symptom of bloating', for at least 2 of the first 4 weeks during the follow-up phase (ie, Weeks 3 through 6).

The results of each trial demonstrate that each of the daily measures of IBS-related symptoms, bloating and abdominal pain demonstrates significant relief with in the primary evaluation period (weeks 3-6) as well as consistent results across all time periods. This finding adds several key observations to what is known about the durable effect of rifaximin on IBS. Namely, that daily questioning, which reduces recall bias presumed to be part of the primary and key secondary endpoints, demonstrates significant and robust finding. Secondly, these finding correlate significantly with the results of the primary and key secondary, yielding interclass correlations which are very strong indicating construct validity (e.g., daily measures show strong relationship and validated measure of disease activity for IBS, weekly SGA). Thirdly, the daily measures were all highly correlated with each other (correlation coefficient of at least 80%). Taken in totality, the results of the primary, key secondary, daily measures of symptoms, bloating and abdominal pain strongly support the reliability, validity, responsiveness, and utility of these outcomes used as endpoints in the studies suggests that each of these questionnaires validates the results from the other.

In addition, using the primary endpoint to assess effect over the entire 3 months of the trial, adequate relief of global IBS symptoms was superior in rifaximin treated as compared to placebo treated patients in each of the trials respectively. This endpoint was tested previously and accepted by the review division, specifically with lotronex, that is, the number of months with adequate relief of IBS symptoms during the entire study duration (typical responses include 0 months, 1 month, 2 months, or 3 months with adequate relief). This approach uses all of the data across the period (12 week/3 months) and demonstrates that 2 weeks of treatment provides 3 months of relief.

The two studies, independently, demonstrate that rifaximin 550 mg TID for 14 days provides statistically significant relief of IBS symptoms during the primary evaluation period (Days 15-42) as measured in:

Weekly IBS Global Symptoms (Primary Endpoint);

Weekly IBS Symptom of Bloating (Key Secondary Endpoint);

IBS Daily Assessment of Symptoms;

Daily IBS Global Symptoms;

Daily IBS Symptom of Bloating; and

Daily IBS Symptom of Abdominal Pain.

Two studies, independently, demonstrate that rifaximin 550 mg TID for 14 days provides statistically significant relief of IBS symptoms during all 3 months as demonstrated by:

Weekly Global IBS Symptoms; and

Daily Global IBS symptoms.

TABLE 21

Subgroup Analysis: Adequate Relief of IBS Symptoms and
IBS Symptom of Bloating by Treatment Group and Gender Gender: Male

|  | Placebo (N = 91) N (%) | Rifaximin 550 mg TID (N = 85) N (%) | p-value |
|---|---|---|---|
| Adequate Relief of IBS symptoms [2] | | | 0.2636 |
| Success | 23 (25.3%) | 28 (32.9%) | |
| Failure | 68 (74.7%) | 57 (67.1%) | |
| Adequate Relief of IBS symptom of Bloating [3] | | | 0.7695 |
| Success | 26 (28.6%) | 26 (30.6%) | |
| Failure | 65 (71.4%) | 59 (69.4%) | |

Gender: Female

|  | Placebo (N = 219) N (%) | Rifaximin 550 mg TID (N = 226) N (%) | p-value |
|---|---|---|---|
| Adequate Relief of IBS symptoms [2] | | | 0.0371 |
| Success | 72 (32.9%) | 96 (42.5%) | |
| Failure | 147 (67.1%) | 130 (57.5%) | |
| Adequate Relief of IBS symptom of Bloating [3] | | | 0.0075 |
| Success | 68 (31.1%) | 98 (43.4%) | |
| Failure | 151 (68.9%) | 128 (56.6%) | |

Note:
Last observation carried forward method (LOCF) was used to handle missing responses. Baseline responses were not carried forward.
[1] p-value is obtained from a Logistic regression model with fixed effects treatment arm.
[2] Subjects achieved success if they answered 'Yes' to the weekly SGA question, 'In the past 7 days, have you had adequate relief of your IBS symptoms', for at least 2 of the first 4 weeks during the follow-up phase (ie, Weeks 3 through 6).
[3] Subjects achieved success if they answered 'Yes' to the weekly SGA question, 'In the past 7 days, have you had adequate relief of your IBS symptom of bloating', for at least 2 of the first 4 weeks during the follow-up phase (ie, Weeks 3 through 6).

TABLE 22

Subgroup Analysis: Adequate Relief of IBS Symptoms and
IBS Symptom of Bloating by Treatment Group and Age Group

|  | Placebo (N = 274) N (%) | Rifaximin 550 mg TID (N = 281) N (%) | p-value |
|---|---|---|---|
| Age Group: <65 | | | |
| Adequate Relief of IBS symptoms [2] | | | 0.0228 |
| Success | 82 (29.9%) | 110 (39.1%) | |
| Failure | 192 (70.1%) | 171 (60.9%) | |
| Adequate Relief of IBS symptom of Bloating [3] | | | 0.0106 |
| Success | 79 (28.8%) | 110 (39.1%) | |
| Failure | 195 (71.2%) | 171 (60.9%) | |
| Age Group: >=65 | | | |
| Adequate Relief of IBS symptoms [2] | | | 0.3862 |
| Success | 13 (36.1%) | 14 (46.7%) | |
| Failure | 23 (63.9%) | 16 (53.3%) | |
| Adequate Relief of IBS symptom of Bloating [3] | | | 0.6838 |

TABLE 22-continued

Subgroup Analysis: Adequate Relief of IBS Symptoms and
IBS Symptom of Bloating by Treatment Group and Age Group

| | Placebo (N = 274) N (%) | Rifaximin 550 mg TID (N = 281) N (%) | p-value |
|---|---|---|---|
| Success | 15 (41.7%) | 14 (46.7%) | |
| Failure | 21 (58.3%) | 16 (53.3%) | |

Note:

Last observation carried forward method (LOCF) was used to handle missing responses. Baseline responses were not carried forward.

[1] p-value is obtained from a Logistic regression model with fixed effects treatment arm.

[2] Subjects achieved success if they answered 'Yes' to the weekly SGA question, 'In the past 7 days, have you had adequate relief of your IBS symptoms', for at least 2 of the first 4 weeks during the follow-up phase (ie, Weeks 3 through 6).

[3] Subjects achieved success if they answered 'Yes' to the weekly SGA question, 'In the past 7 days, have you had adequate relief of your IBS symptom of bloating', for at least 2 of the first 4 weeks during the follow-up phase (ie, Weeks 3 through 6).

TABLE 23

Subgroup Analysis: Adequate Relief of IBS Symptoms and
IBS Symptom of Bloating by Treatment Group and Race

Race: White

| | Placebo (N = 292) N (%) | Rifaximin 550 mg TID (N = 280) N (%) | p-value |
|---|---|---|---|
| Adequate Relief of IBS symptoms [2] | | | 0.0341 |
| Success | 89 (30.5%) | 109 (38.9%) | |
| Failure | 203 (69.5%) | 171 (61.1%) | |
| Adequate Relief of IBS symptom of Bloating [3] | | | 0.0172 |
| Success | 87 (29.8%) | 110 (39.3%) | |
| Failure | 205 (70.2%) | 170 (60.7%) | |

Race: Non-White

| | Placebo (N = 18) N (%) | Rifaximin 550 mg TID (N = 31) N (%) | p-value |
|---|---|---|---|
| Adequate Relief of IBS symptoms [2] | | | 0.3074 |
| Success | 6 (33.3%) | 15 (48.4%) | |
| Failure | 12 (66.7%) | 16 (51.6%) | |
| Adequate Relief of IBS symptom of Bloating [3] | | | 0.6691 |
| Success | 7 (38.9%) | 14 (45.2%) | |
| Failure | 11 (61.1%) | 17 (54.8%) | |

Note:

Last observation carried forward method (LOCF) was used to handle missing responses. Baseline responses were not carried forward.

[1] p-value is obtained from a Logistic regression model with fixed effects treatment arm and analysis center.

[2] Subjects achieved success if they answered 'Yes' to the weekly SGA question, 'In the past 7 days, have you had adequate relief of your IBS symptoms', for at least 2 of the first 4 weeks during the follow-up phase (ie, Weeks 3 through 6).

[3] Subjects achieved success if they answered 'Yes' to the weekly SGA question, 'In the past 7 days, have you had adequate relief of your IBS symptom of bloating', for at least 2 of the first 4 weeks during the follow-up phase (ie, Weeks 3 through 6).

TABLE 24

Subgroup Analysis: Adequate Relief of IBS Symptoms
and IBS Symptom of Bloating by Treatment Group and
IBS Sub-type IBS Subtype: Diarrhoea-predominant

IBS Subtype: Diarrhoea-predominant

| | Placebo (N = 292) N (%) | Rifaximin 550 mg TID (N = 280) N (%) | p-value |
|---|---|---|---|
| Adequate Relief of IBS symptoms [2] | | | 0.0337 |
| Success | 87 (31.4%) | 111 (40.1%) | |
| Failure | 190 (68.6%) | 166 (59.9%) | |
| Adequate Relief of IBS symptom of Bloating [3] | | | 0.0928 |
| Success | 90 (32.5%) | 109 (39.4%) | |
| Failure | 187 (67.5%) | 168 (60.6%) | |

IBS Subtype: Alternating-predominant

| | Placebo (N = 18) N (%) | Rifaximin 550 mg TID (N = 31) N (%) | p-value |
|---|---|---|---|
| Adequate Relief of IBS symptoms [2] | | | 0.2202 |
| Success | 8 (24.2%) | 13 (38.2%) | |
| Failure | 25 (75.8%) | 21 (61.8%) | |
| Adequate Relief of IBS symptom of Bloating [3] | | | 0.006 |
| Success | 4 (12.1%) | 15 (44.1%) | |
| Failure | 29 (87.9%) | 19 (55.9%) | |

Note:

Last observation carried forward method (LOCF) was used to handle missing responses. Baseline responses were not carried forward.

[1] p-value is obtained from a Logistic regression model with fixed effects treatment arm.

[2] Subjects achieved success if they answered 'Yes' to the weekly SGA question, 'In the past 7 days, have you had adequate relief of your IBS symptoms', for at least 2 of the first 4 weeks during the follow-up phase (ie, Weeks 3 through 6).

[3] Subjects achieved success if they answered 'Yes' to the weekly SGA question, 'In the past 7 days, have you had adequate relief of your IBS symptom of bloating', for at least 2 of the first 4 weeks during the follow-up phase (ie, Weeks 3 through 6).

Example 6: Analysis of Two Studies after 3 Months

Studies were designed to evaluate the efficacy of oral rifaximin at 550 mg TID in providing adequate relief from diarrhea-predominant IBS (dIBS) symptoms over three months. A measure of efficacy is based on subjects' answers to the Weekly Subject Global Assessment (SGA) questions over the study duration in relation to their IBS symptoms.

The two studies, independently, demonstrate that rifaximin 550 mg TID for 14 days provides statistically significant relief of IBS symptoms during the primary evaluation period and the 10 weeks of monitoring after the administration period ends. The results are presented in Table 25 below.

TABLE 25A

| | | | | Endpoints |
|---|---|---|---|---|
| Global IBS symptoms | 31% vs 41% (p = 0.0125) | 32% vs 41% (p = 0.0263) | 32% vs 41% (p = 0.0008) | At least 2 out of 4 weeks adequate relief of IBS symptoms during weeks 3 through 6 (weekly question) |
| AUC in abdominal pain during PEP | P = 0.0128 | P = 0.0328 | P = 0.0017 | |

TABLE 25B

Endpoints for Abdominal Pain (Change from baseline in median)

| Endpoint | Study | Study 2 | Combined | Description |
|---|---|---|---|---|
| Abdominal pain reduction of 1 point in median | 52% vs 63% (p = 0.0039) | 53% vs 62% (p = 0.0382) | 53% vs 63% (p = 0.0005) | Responder is defined as who had reduction of 1 point in the weekly median score of abdominal pain compared to baseline for at least 2 weeks during PEP. Baseline median is based on the last three diary entries prior to the first dose date. Post-baseline weekly median is based on all diary entries in that week. |
| Abdominal Pain reduction of 2 point in median | 33% vs 37% (p = 0.3155) | 30% vs 41% (p = 0.0049) | 32% vs 39% (p = 0.0064) | See above |
| Abdominal Pain reduction of 3 point in median | 19% vs 22% (p = 0.3443) | 17% vs 21% (p = 0.2329) | 18% vs 21% (p = 0.1333) | See above |
| Daily abdominal pain <2 | 32% vs 40% (p = 0.0373) | 31% vs 39% (p = 0.0383) | 31% vs 39% (p = 0.0036) | Responder is defined as who had daily abdominal pain <2 for at least 50% of days in a given week for at least 2 weeks during PEP. |
| Overall reduction of median weekly abdominal pain by >=25% | 52% vs 63% (p = 0.0051) | 52% vs 62% (p = 0.0170) | 52% vs 62% (p = 0.0003) | Responder is defined as whose weekly median abdominal pain score dropped by at least 25% comparing to baseline median pain score for at least 2 weeks during PEP. Baseline median is based on the last three diary entries prior to the first dose date. Post-baseline weekly median is based on all diary entries in that week. |
| Overall reduction of median weekly abdominal pain by >=50% | 34% vs 44% (p = 0.0080) | 35% vs 44% (p = 0.0117) | 34% vs 44% (p = 0.0003) | See above |
| Overall reduction of median weekly abdominal pain by >=75% | 19% vs 23% (p = 0.2169) | 17% vs 20% (p = 0.3648) | 18% vs 21% (p = 0.1334) | See above |
| Abdominal pain reduction of 1 point in mean | 41% vs 52% (p = 0.0065) | 43% vs 52% (p = 0.0156) | 42% vs 52% (p = 0.0003) | Responder is defined as who had reduction of 1 point in the weekly mean score of abdominal pain compared to baseline for at least 2 weeks during PEP. |
| Abdominal Pain reduction of 2 point in mean | 18% vs 26% (p = 0.0181) | 18% vs 25% (p = 0.0198) | 18% vs 25% (p = 0.001) | See above |
| Abdominal Pain reduction of 3 point in mean | 6% vs 7% (p = 0.4475) | 6% vs 7% (p = 0.4828) | 6% vs 7% (p = 0.3676) | See above |

TABLE 25B-continued

Endpoints for Abdominal Pain (Change from baseline in median)

| Endpoint | Study | Study 2 | Combined | Description |
|---|---|---|---|---|
| Daily abdominal pain <2 | 32% vs 40% (p = 0.0373) | 31% vs 39% (p = 0.0383) | 31% vs 39% (p = 0.0036) | Responder is defined as who had daily abdominal pain <2 for at least 50% of days in a given week for at least 2 weeks during PEP. |
| Overall reduction of mean weekly abdominal pain by >=25% | 47% vs 56% (p = 0.0125) | 47% vs 58% (p = 0.0036) | 47% vs 57% (p = 0.0001) | Responder is defined as whose weekly mean abdominal pain score dropped by at least 25% comparing to baseline mean pain score for at least 2 weeks during PEP. |
| Overall reduction of mean weekly abdominal pain by >=50% | 28% vs 36% (p = 0.0280) | 29% vs 35% (p = 0.1101) | 28% vs 35% (p = 0.0075) | See above |
| Overall reduction of mean weekly abdominal pain by >=75% | 10% vs 14% (p = 0.1045) | 11% vs 14% (p = 0.3617) | 11% vs 14% (p = 0.0780) | See above |
| IBS symptom of Bloating | 29% vs 40% (p = 0.0045) | 32% vs 41% (p = 0.0167) | 30% vs 40% (p = 0.0002) | At least 2 out of 4 weeks adequate relief of IBS symptom of bloating during weeks 3 through 6 (weekly question) |
| Durable response during the entire 3-month study period |  |  |  |  |
| Global IBS symptoms (weekly) | P = 0.0477 (See Table 14.2.5a) | P = 0.0053 (See Table 14.2.5a) | P = 0.0007 (See Table 3.05a) | Number of months that subjects are monthly responders during the 3-month study period. Monthly responders are defined as at least 2 out of 4 weeks adequate relief. |
| IBS symptom of bloating (weekly) | P = 0.1042 (See Table 14.2.5a) | P = 0.0031 (See Table 14.2.5a) | P = 0.0011 (See Table 3.05a) | See above |
| Abdominal pain (daily) | P = 0.0495 (See Table 14.2.6a) | P = 0.0435 (See Table 14.2.6a) | P = 0.0118 (See Table 3.06a) | Number of months that subjects are monthly responders during the 3-month study period. Monthly responders are defined as at least 2 out of 4 weeks relief of abdominal pain. Weekly relief is defined as subjects who had 0 (not at all) or 1 (hardly) 50% of days within a given week, OR 0, 1 or 2(somewhat) 100% of days within a given week. |

TABLE 25

Definitions

| Study Population | Study 1 | Study 2 | Definition |
|---|---|---|---|
| Intent to Treat | 623 | 635 | Randomized subjects who took at least one dose of the study drug. |
| Modified Intent to Treat | 461 (73%) | 501 (78%) | Randomized subjects who took at least one dose of the study drug and met the following criteria: Compliance rate is at least 90% Had at least 4 weeks follow-up after the end of dosing. |

The study endpoints of the studies were Global IBS symptoms and AUC in abdominal pain during the study.

Other Endpoints Measured were:

Reduction of abdominal pain by 1 point from baseline in mean;

Reduction of abdominal pain by 2 point from baseline in mean;

Reduction of abdominal pain by 3 point from baseline in mean;

Daily abdominal pain of <2 from baseline in mean;

Overall reduction of median weekly abdominal pain by >=25% from baseline in mean;

Overall reduction of median weekly abdominal pain by >=50% from baseline in mean;

Overall reduction of median weekly abdominal pain by >=75% from baseline in mean;

Reduction of abdominal pain by 1 point from baseline in mean;

Reduction of abdominal pain by 2 point from baseline in mean;

Reduction of abdominal pain by 3 point from baseline in mean;

Daily abdominal pain of <2 from baseline in mean;

Overall reduction of median weekly abdominal pain by >=25% from baseline in mean;

Overall reduction of median weekly abdominal pain by >=50% from baseline in mean;

Overall reduction of median weekly abdominal pain by >=75% from baseline in mean;

IBS Symptom of bloating;
Durable Response During the Three Month Study
Global IBS symptoms (weekly);
IBS symptom of bloating (weekly);
Abdominal pain (daily).

Also, the proportions of subjects with adequate relief are set forth in Tables 25, 25A and 25B.

The two studies demonstrate that rifaximin 550 mg TID for 14 days provides statistically significant relief of IBS symptoms over a three month period as demonstrated by evaluating the primary and secondary endpoints.

The primary and secondary endpoints evaluated in this study were the effect of treatment on the percentage of subjects who reported adequate relief of Global IBS symptoms, reduction in abdominal pain and the adequate relief of IBS symptom of bloating. These results are shown in Appendices. The data demonstrates that more subjects taking rifaximin had adequate relief of Global IBS symptoms, abdominal pain and of bloating.

INCORPORATION BY REFERENCE

The contents of all references, patents, pending patent applications and published patents, cited throughout this application are hereby expressly incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of treating bloating associated with diarrhea-predominant IBS in a subject 65 years old or older, said method comprising administering, for between 14 days and 24 months, 550 mg of rifaximin TID, to the subject, thereby treating bloating associated with diarrhea-predominant IBS in the subject 65 years old or older.

2. The method of claim 1, wherein the treating of bloating comprises a reduction of bloating.

3. The method of claim 2, wherein the reduction of bloating is achieved following 7 days of the administration of the rifaximin.

4. The method of claim 2, wherein the reduction of bloating comprises an affirmative response from a subject if asked whether they have had a reduction in bloating.

5. The method of claim 1, further comprising treating one or more symptoms associated with diarrhea-predominant IBS selected from cramping, pain, diarrhea, constipation, lumpy stool, watery stool, frequent stool production, abdominal pain, abdominal discomfort, urgency, and tenesmus.

6. The method of claim 2, wherein the reduction in bloating is a reduction as compared with baseline.

7. The method of claim 6, wherein baseline is established prior to treatment.

8. The method of claim 7, wherein the reduction in bloating is achieved following 7 days of the administration of the rifaximin.

9. The method of claim 8, wherein the reduction in bloating comprises an affirmative response from a subject if asked whether they have had a reduction in bloating.

* * * * *